United States Patent
Sanz Merodio et al.

(10) Patent No.: US 11,324,653 B2
(45) Date of Patent: May 10, 2022

(54) EXOSKELETON FOR ASSISTING HUMAN MOVEMENT

(71) Applicants: CONSEJO SUPERIOR DE INVESTIGACIONES CIENTIFICAS (CSIC), Madrid (ES); UNIVERSIDAD POLITECNICA DE MADRID, Madrid (ES); MARSI BIONICS, S.L., Madrid (ES)

(72) Inventors: Daniel Sanz Merodio, Madrid (ES); Manuel Javier Cestari Soto, Madrid (ES); Elena García Armada, Madrid (ES); Xavier Carrillo De Hijes, Madrid (ES)

(73) Assignees: MARSI BIONICS S.L., Madrid (ES); CONSEJO SUPERIOR DE INVESTIGACIONES CIENTIFICAS (CSIC), Madrid (ES); UNIVERSIDAD POLITECNICA DE MADRID, Madrid (ES)

( * ) Notice: Subject to any disclaimer, the term of this patent is extended or adjusted under 35 U.S.C. 154(b) by 672 days.

(21) Appl. No.: 15/531,266

(22) PCT Filed: Nov. 25, 2015

(86) PCT No.: PCT/ES2015/070855
§ 371 (c)(1),
(2) Date: May 26, 2017

(87) PCT Pub. No.: WO2016/083650
PCT Pub. Date: Jun. 2, 2016

(65) Prior Publication Data
US 2017/0340504 A1 Nov. 30, 2017

(30) Foreign Application Priority Data
Nov. 27, 2014 (ES) .............................. ES201431763

(51) Int. Cl.
*A61H 3/00* (2006.01)
*A61H 1/02* (2006.01)
(Continued)

(52) U.S. Cl.
CPC ............. *A61H 1/0262* (2013.01); *A61F 5/01* (2013.01); *A61H 1/02* (2013.01); *A61H 3/00* (2013.01);
(Continued)

(58) Field of Classification Search
CPC ................ A61H 3/00; A61H 2003/005; A61H 2003/007; A61H 2003/008; A61H 1/0262;
(Continued)

(56) References Cited

U.S. PATENT DOCUMENTS 7,153,242 B2 12/2006 Goffer
7,947,004 B2 5/2011 Kazerooni et al.
(Continued)

FOREIGN PATENT DOCUMENTS

| ES | 2 491 218 | 9/2014 |
| WO | 2012/027336 | 3/2012 |
| WO | 2013/019749 | 2/2013 |

OTHER PUBLICATIONS

International Search Report dated Feb. 19, 2016 in corresponding International Application No. PCT/ES2015/070855.

*Primary Examiner* — Christopher D. Prone
(74) *Attorney, Agent, or Firm* — Wenderoth, Lind & Ponack, L.L.P.

(57) ABSTRACT

The invention relates to an exoskeleton for assisting human movement, which can be fitted to the user in terms of dimensions, tension and ranges of joint motion, either manually or automatically. The exoskeleton can be fitted to the user in the anteroposterior direction in the sagittal plane, with the user in a horizontal or sitting position, without (Continued)

requiring a functional transfer. The exoskeleton has a modular design which is compatible with human biomechanics and reproduces a natural and physiological movement in the user, with up to 7 actuated and controlled degrees of movement per limb, ensuring that the user maintains equilibrium during locomotion.

14 Claims, 18 Drawing Sheets

(51) Int. Cl.
 B25J 9/00 (2006.01)
 A61F 5/01 (2006.01)
(52) U.S. Cl.
 CPC ............. *B25J 9/00* (2013.01); *B25J 9/0006* (2013.01); *A61H 2201/0107* (2013.01); *A61H 2201/1207* (2013.01); *A61H 2201/1223* (2013.01); *A61H 2201/1238* (2013.01); *A61H 2201/5007* (2013.01); *A61H 2201/5038* (2013.01); *A61H 2201/5064* (2013.01); *A61H 2201/5071* (2013.01); *A61H 2201/5084* (2013.01); *A61H 2230/105* (2013.01); *A61H 2230/605* (2013.01)

(58) Field of Classification Search
 CPC ...... A61H 2201/149; A61H 2201/1628; A61H 2205/088; B25J 9/0006
 See application file for complete search history.

(56) References Cited

U.S. PATENT DOCUMENTS

| 8,057,410 | B2 | 11/2011 | Angold et al. |
| 8,096,965 | B2 | 1/2012 | Goffer et al. |
| 10,398,617 | B2 * | 9/2019 | Simon ..................... A61H 3/00 |
| 2006/0052731 | A1 | 3/2006 | Shimada et al. |
| 2007/0056592 | A1 | 3/2007 | Angold et al. |
| 2007/0123997 | A1 | 5/2007 | Herr et al. |
| 2011/0066088 | A1 | 3/2011 | Little et al. |
| 2012/0101415 | A1 | 4/2012 | Goffer et al. |
| 2014/0213951 | A1 | 7/2014 | Pietrusisnki et al. |
| 2015/0272809 | A1 * | 10/2015 | Accoto ................ A61H 1/0237 623/31 |

\* cited by examiner

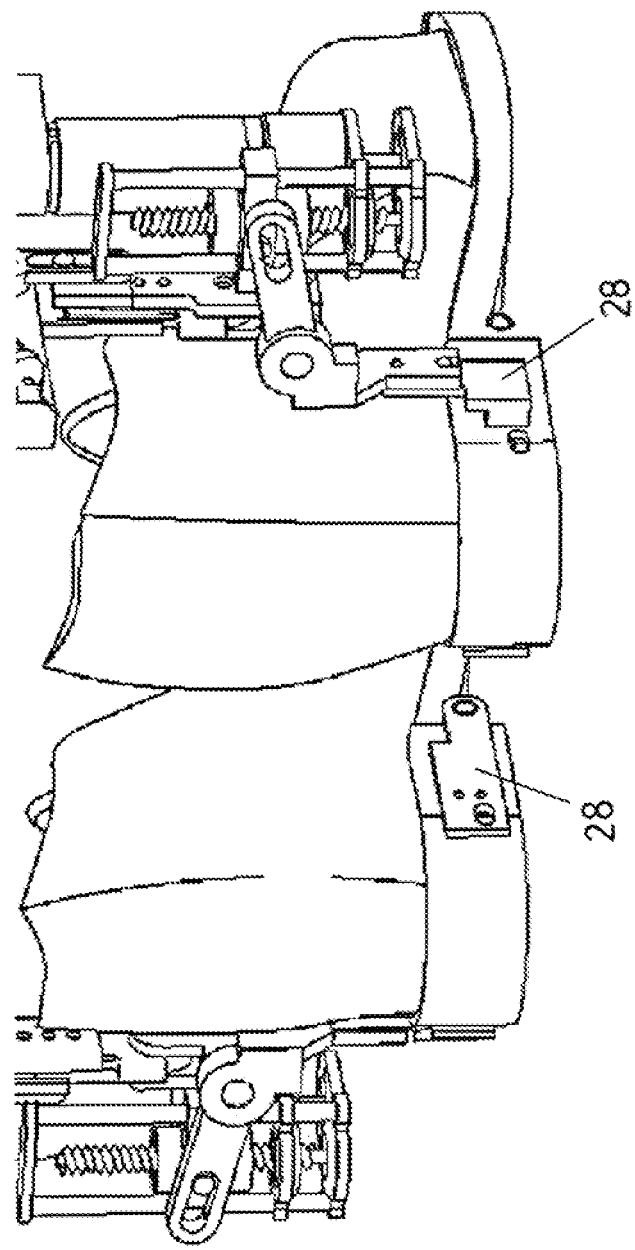

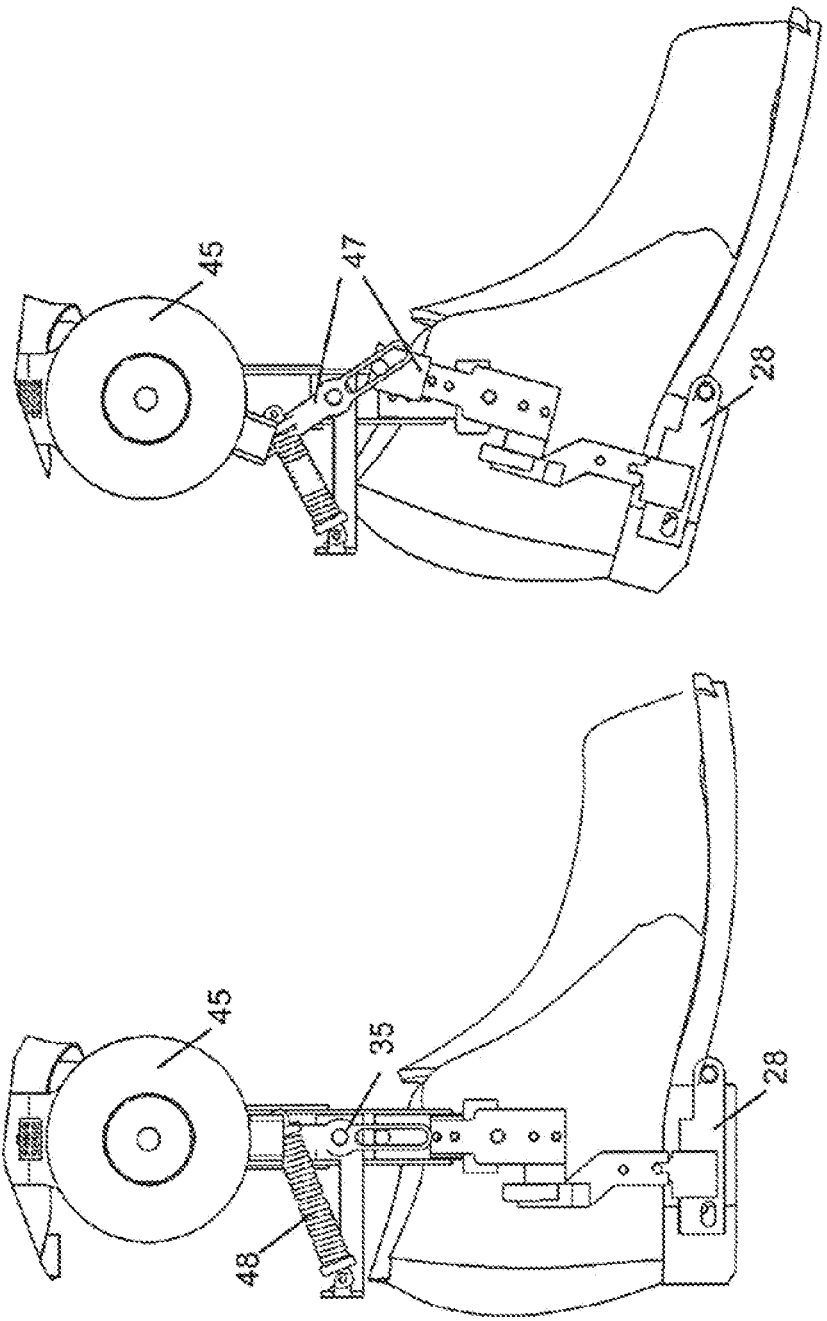

EXOSKELETON FOR ASSISTING HUMAN MOVEMENT

OBJECT OF THE INVENTION

The invention relates to an exoskeleton for assisting human movement, which can be fitted to the user in terms of dimensions, tension and ranges of joint motion, either manually or automatically. The exoskeleton can be fitted to the user from front to back in the anteroposterior direction in the sagittal plane, with the user in a horizontal or sitting position, without requiring a functional transfer of the user to the exoskeleton.

The object of the invention is an exoskeleton for assisting human movement that has a modular design, compatible with human biomechanics and that reproduces a natural and physiological movement in the user, with up to 7 actuated and controlled degrees of movement per limb, ensuring that the user maintains equilibrium during locomotion without using sustaining auxiliary elements.

BACKGROUND OF THE INVENTION

People with disabling neurological disorders, such as spinal injuries, neuromuscular disorders, cerebral paralysis, etc. suffer partial or total mobility impairment and in many cases sensory impairment. The disruption in mobility affects functional independence to carry out every day activities and negatively affects various basic physiological functions causing, among others, urinary and fecal incontinence, sexual dysfunction and cardiovascular problems. The social impact often entails loss of employment, separation from a partner, among others. This group of factors has an effect on the self-esteem of the person and causes severe psychological problems.

Neurological rehabilitation pursues muscular reeducation and gait training, making use of orthoses, canes, crutches, walkers and other orthopedic devices. Rehabilitation methods can be improved by using active orthotic devices, based on the robotization of passive orthoses by acting on their joints with controlled motors in order to generate the natural movement of the human gait. These devices may be limited to movement on a treadmill, as part of the rehabilitation machinery of a hospital, or they may be portable, allowing in this latter case daily rehabilitation at home, and ideally could even substitute the wheelchair in daily life, allowing for the recovery of basic physiological functions, and even facilitating social and job reinsertion of the patient.

The latter devices, active portable orthoses, also called wearable exoskeletons, are mechanical devices, made up of rigid segments joined to each other by means of motorized joints that couple to the limbs of a user by means of generally rigid posterior braces, manufactured to fit the patient and coupled to the limbs of the user by means of bands with Velcro or buckles. The mechanical structure is usually custom-made to fit a patient and lacks the flexibility to be used in other patients or even in the same user when the disease has evolved significantly. Thus, they are non-transferable devices and for short-term use. Using automatic motor control techniques, these exoskeletons are controlled in order to generate a joint movement equivalent to that of a healthy person, and to transmit the movement to the extremity to which they are coupled. The energy source necessary to feed the motors and the electronic gear must be included on board and are usually located in the back of the device, which tends to be an obstacle for sitting or lying down with the exoskeleton, in addition to significantly hindering the recharging or replacement of the batteries.

One of the main technological challenges facing wearable exoskeletons is finding a compromise between a lightweight and compact structure that facilitates handling by a user, who usually has muscular weakness, and on the other hand a robotic system that implements a physiologically complete biomechanical model. The second is accomplished by increasing the number of degrees of movement of the robotic structure, in order to make it resemble the human biomechanical model, but the weight and volume that the actuators and transmission systems impose on the structure multiply with the number of active joints and the result is a mechanical structure that is too heavy to be functional. The issue is, while there are no actuators with the high power/weight ratio required to achieve both of these objectives, which of these should take precedence. Evidently, if it relates to developing devices that allow the neuromuscular rehabilitation of the limbs of a patient, the movement that the device rehabilitates must be compatible with human biomechanics. Generating other kinds of movements may ultimately be harmful for the neuromuscular system. Biomechanics indicate that the leg of a human can be modeled with 7 degrees of movement, however in the study of locomotion, an additional degree of freedom appears: the knee rotation upon finishing the support phase. Thus, a model with 8 degrees of freedom adapts optimally to human biomechanics.

1. Hip flexion/extension
2. Hip abduction/adduction
3. Hip rotation
4. Knee flexion/extension
5. Knee rotation
6. Ankle flexion/extension
7. Ankle eversion/inversion
8. Ankle rotation It is clear that the closer the mechanical model of the exoskeleton gets to these degrees of freedom or movement, the more natural and physiologically healthy the gait imposed on the patient will be. But, it should also to be noted that some of these degrees of freedom have a fundamental role in human movement. The synchronized flexion/extension movement of the three joints in the sagittal plane generates the gait in this plane. Perhaps, the most significant is the role of two of the degrees of freedom of the ankle.

7 muscles take part in plantar flexion or ankle flexion movement: soleus, gastrocnemius, peroneus longus and brevis, tibialis posterior and flexor digitorum longus, which together with the Achilles tendon are able to impose a power of 500 W (for a male weighing 70 kg) in the moment the foot lifts off from the ground. The body uses this energy not only to lift the foot off the ground and prevent any kind of collision during the forward foot transfer phase, but also to propel the entire center of mass forwards. Without it, the gait loses its natural energy balance and also the ability to maintain the anteroposterior equilibrium of the body.

Movements in the transverse plane, although not as significant in amplitude as the movements in the sagittal plane, also carry out a relevant function. The abduction/adduction movement of the hip enables balancing body weight from one leg to the other during the double support phase, while enabling direction changes during gait. The eversion/inversion movement of the ankle allows for the equilibrium of the body in the lateral plane.

Most of known exoskeletons sacrifice locomotive function in favor of a design with low complexity and cost. Document U.S. Pat. No. 7,153,242B2 describes a lower limb exoskeleton made up of rigid segments and braces, joined by two rotational joints in each leg, one in the hip and another in the knee, that are controlled by linear or rotational actuators, generating movement solely in the sagittal plane and conferring a mobility of two degrees of freedom for each leg, which does not allow lateral movements or stabilization of the equilibrium of the user during gait. The exoskeleton incorporates a passive ankle joint, with a spring for carrying out dorsiflexion during the foot transfer phase and avoid impact against the ground. The option of passively activating the ankle has negative effects on gait generation, since it prevents any motor capacity in the ankle in the impulse prior to the foot transfer phase.

This exoskeleton requires the use of crutches to maintain the stability or equilibrium of the patient in locomotion, and leaves any movement on the lateral plane up to the user, such as changes in direction or even the distribution of weight from one leg to the other in stance changes. This restricts its use to patients with muscle strength in the arms and lateral mobility in the trunk. The movement is commanded by means of thoracic movements in the sagittal plane of the user, reason for which its use is also limited to patients with this capacity of movement. Thus, it relates to a device exclusively for use in spinal cord injuries below the sixth dorsal vertebra (T6) with paraplegia. The energy source is located in the rear portion of the device, lying on the patient's back, while the electronic units are located in the front portion. The device can generate a variety of movement patterns: gait on flat ground and in a straight line, up or down stairs, and transitions from sitting to standing and vice versa, however all the gait programs are recorded for a specific patient and are reproduced in the actuators, preventing any capacity to adapt the pace differently from the pre-established settings. Later improvements of this invention, described in documents US2012/0101415A1 and U.S. Pat. No. 8,096,965B2 add the possible use combined with Functional Electrical Stimulation (FES) and a safety module that reviews the state of all of the electrical components in order to prevent any operational malfunctions.

Documents U.S. Pat. Nos. 7,947,004B2 and 8,057,410B2 describe a very similar exoskeleton, although it incorporates some important improvements. Although it also only has two actuated degrees of freedom per leg in the sagittal plane, this exoskeleton incorporates passive joints in the hip and ankle on the lateral plane, which enable a slight abduction and adduction movement, and it incorporates a torsional spring in the upper segment of the leg, enabling slight hip rotation, which in turn causes greater comfort for the user during gait and better adaptation of the orthosis to the physical characteristics of the patient. Even so, the lack of actuated degrees of freedom results in an insufficient gait from a medical point of view, since it restricts controlled movement in the sagittal plane, prevents equilibrium control, and therefore requires additional sustaining elements such as canes, and cancels out the energy contribution of the ankle joint in the impulse prior to the foot transfer phase. This exoskeleton can be coupled to the shoe of the user, either on the outside, or on the inside like an insert introduced in the shoe although this tends to require modifying the footwear. The gait is controlled in a joint manner based on prerecorded patterns, and the phases of the locomotion cycle are distinguished by means of sensors under the feet that determine the reaction force of the ground.

The knee joint is modeled in biomechanics as a single rotation in the sagittal plane. However, this is a simplification that eliminates some of the functions of this joint that is one of the most complex of the human body, actually being a capsule made up of three joints: tibiofemoral joint (between the condyles of the femur and the tibia), patellofemoral joint (between the trochlea of the femur and the articular face of the patella) and the proximal tibioperoneal joint. Even though the main movement of the knee is flexion-extension in the sagittal plane, the last two knee joints allow the patella to slightly slide up or down and from the inside to the outside. To incorporate these movements, some more realistic biomechanical models incorporate a polycentric shaft in the sagittal plane that is displaced by means of a mechanism of four bars.

The ankle joint in the sagittal plane plays a fundamental role in human gait. It provides the greatest instantaneous strength to the human body during the impulse phase when the foot lifts off from the ground and proceeds to the forward transfer phase of the leg. Known devices incorporate an elastic system that only flexes the ankle in order to clear the foot from the ground and prevent it from impacting it during the transfer. However, this eliminates the energy contribution that the body needs in order to maintain locomotion in an energy efficient way.

International application WO2012/027336A1 includes operational stand-up and sit-down functions, as well as a state machine for controlling the transition between these functions and the walking mode, and completes the device with an auxiliary support element (walker or crutches) in order to provide the lateral stability that the exoskeleton does not provide. Remote controls or joysticks are incorporated in these auxiliary devices that allow for controlling the speed of the exoskeleton. Communication between the exoskeleton and the auxiliary device is wireless. Finally, it provides for the incorporation of a cerebral interface for the control of the exoskeleton, and a voice recognition system.

Document US2011/0066088A1 describes a lower limb exoskeleton with five degrees of freedom per leg, including sagittal and lateral actuation in the ankle and in the abduction/adduction of the hip, which enables the movement of the patient both on the sagittal as well as the lateral plane, and it further allows for controlling and maintaining the stability of the patient without having to use auxiliary devices like crutches or walkers. The mechanical structure is extensible to fit the size of the user. The batteries are placed in the rear portion of the exoskeleton, remaining at around kidney height, which, even though they are replaceable, hinders this operation for the user. This device incorporates a pelvic harness that supports the weight of the patient, opening its use to patients with weak bones. The use of this harness has the disadvantage of inducing an external rotation of the hips, which is subsequently forcibly corrected with the clamps of the exoskeleton in the femur and tibia, which causes pathological joint stress. Pelvic harnesses are discouraged for gait. As a successful biomechanical element, it has a polycentric-type knee, more similar to the human knee (widely used in knee prosthesis). Despite this characteristic, this design lacks hip rotation, fundamental for imposing the trajectory of the pressure center in the sole of the foot corresponding to a healthy gait.

The structure of this device incorporates water and dust protection. Its sensory system includes inertia units, incremental optic gauges for joint position and pressure sensors in the soles of the feet. A laser or distance sensor allows for determining the profile of the ground in order to generate suitable walking modes. Even though it is the only exoskeleton with the ability to control the stability or equilibrium of the patient, the disadvantage of this exoskeleton is its low speed, failing to reach gait speeds above 0.05 m/s, which makes it not very useful. This is due to the need to generate highly elevated joint torques in order to guarantee the stability of the system, which proportionally reduces the joint speed based on a transmission ratio, which is necessary given the power limit of the actuators.

Document WO2013/019749A1 describes a very generic exoskeleton, with very similar features to those described previously, although it does not provide for the control of the stability of the exoskeleton-user assembly understood as the control of posture equilibrium during locomotion. The reference made in the document to stability control refers to the ability of the device to support the person on standing still or in a stable standing position, as far as the required forces are concerned. This document further describes the interface system between the user and the exoskeleton, which can be carried out by means of any system capable of acquiring commands from the user.

Document US2007/0123997A1 describes a lower limb exoskeleton design for energy saving during locomotion. The exoskeleton is designed with three degrees of freedom per leg, thus generating movement only in the sagittal plane, but only uses one actuator in the hip joint. Based on biomechanical studies, a controllable absorber-type energy-dissipating element in the knee is proposed, and an elastic element in order to actuate the ankle. The combination of these three elements: motor, absorber and spring generates a gait pattern very similar to the biological pattern, with minimal energy consumption. Another novelty is the incorporation of a rigid pelvic harness, similar to a bicycle saddle, to sustain the user's weight. This solution improves the problem of the conventional pelvic harness.

There are further examples of portable exoskeletons for locomotive assistance that are made up of one or more kinematic chains of segments and joints of any number of degrees of freedom, the dimensions of which segments dimensions can be adjustable in length, and that couples to the human body and its limbs (legs, arms or segments) by means of a fastening system based on rigid or semi-rigid rear braces, belts, straps, Velcro fasteners, buckles etc. and being able to include a pelvic or thoracic belt or harness.

All of these devices require an excessive prior fitting by specialized staff, both of the mechanical structure that must be perfectly coupled to the user, and of the movement control methods, which are based on monitoring of specific reference patterns for a patient. This lack of flexibility in the designs and movement control methods greatly hinders the widespread use of exoskeletons. On the one hand, custom-made manufacturing makes mass production impossible and consequently prevents lowering of costs of the final product in order to reach the user. On the other hand, it is important to keep in mind the variability of the symptoms in the same user throughout their life and in the course of each day. For example, patients suffering from spasticity (joint stiffness) will progressively reduce the degree of spasticity with daily rehabilitation, so they would have to change devices or adjust it appropriately as the pathology evolves. According to neurological rehabilitation professionals, a patient's spasticity can undergo significant variations during a rehabilitation exercise in a short period of time.

As seen in the review of the state of the art, none of the known embodiments are able to control the equilibrium of the exoskeleton-user assembly during gait at a normal walking speed. For this reason, it is necessary to use additional elements such as canes or walkers that help the user to maintain equilibrium. This restricts the number of potential users to those that have strength and mobility in the upper limbs, while keeping the hands busy preventing them from being used for any other function. It is desirable for the exoskeleton to maintain equilibrium in a controlled manner without the aid of additional elements.

It is necessary to have exoskeletons that are automatically fitted to each user, not only in dimensions but also especially in features, in the degree of mobility provided depending on the user's own mobility, and in controlling the movement of each joint and the gait. This fitting should not require specialized staff and should be as automatic as possible, so that it requires minimal intervention by the user or the rehabilitating physician.

The fastening and fitting of the exoskeleton to the human body are especially relevant in the correct transmission of movement to the user, while they must guarantee the health of the same, without oppressing or causing any damage. Most of the developments mentioned in the state of the art incorporate rear rigid braces on the limps, fitted to the user by means of Velcro fasteners. Some developments further include a pelvic harness that ensures the transfer of part of the user's weight to the exoskeleton. According to physiotherapy experts, the use of these harnesses prevents natural gait, since upon causing the groin openings of the user it generates external rotation of the hip, which is artificially corrected by the device when aligning the knees. Both anti-physiological effects can cause damage during gait and therefore medical specialists discourage the use of the pelvic harness for gait.

All the lower limb exoskeletons described in the state of the art require a functional transfer of the user from their wheelchair or from the bed to the exoskeleton. This prevents autonomy and independence of the user in their daily use. This is mainly due to the fastening mechanisms of the exoskeleton to the user's body, these having rigid braces in the rear portion of the thigh and shin in order to ensure support of the limb. Furthermore, the lumbar reinforcement, which is indispensable in any orthosis from the waist down through medical determination, is located in the rear portion of the exoskeleton. Therefore, it is not possible to place the exoskeleton from the anterior to the posterior position since the lumbar reinforcement and the braces get in the way.

The mechanical structure of the exoskeleton must allow and never impede the normal physiological position of the longitudinal axes of the parts that are coupled to the lower limbs of the user. The feet, in a physiologically standing position are at an angle to each other, such that during gait, the distance between the heels on the lateral plane is very small and approximately a third of the distance between the tips of the toes. For this to be accomplished normally, the cervical diaphysiary angle of the femur neck and the condylar angle formed between the femur and tibia have normal values.

In addition, since these are exoskeletons to aid rehabilitation of patients with anti-physiological gait, the mechanical structure must allow for fitting in people with anatomical anomalies, like hips with abnormal cervical diaphysiary angles or bow-leggedness and knock knees.

None of the devices known in the state of the art fulfill this anatomical function, having cervical angles of 90° and condylar angles of 0°, which in no case correspond to a physiological gait and therefore generate an abnormal gait in patients without anomalies and they may not be used in patients with anomalies.

The exoskeleton for assisting human movement of the present invention resolves all of the previously mentioned inconveniences.

DESCRIPTION OF THE INVENTION

The present invention relates to an exoskeleton for assisting human movement, which can be fitted to the user in terms of dimensions, tension and ranges of joint motion, either manually or automatically. The exoskeleton can be fitted to the user from front to back in the anteroposterior direction in the sagittal plane, with the user in a horizontal or sitting position, without requiring a functional transfer of the user to the exoskeleton. The exoskeleton has a modular design, which is compatible with human biomechanics and reproduces a natural and physiological movement in the user, with up to 7 actuated and controlled degrees of movement per limb, ensuring that the user maintains equilibrium during locomotion without using sustaining auxiliary elements.

The exoskeleton for assisting human movement of the present invention comprises a mechanical structure comprising segments joined by joints that enable relative movement between two or more successive segments in order to move the limbs of the user. The mechanical structure is modular, in other words, it can be made up of one or two independent limbs that can be coupled, and to which any other device can be coupled like a robotic arm, tool or even another upper limb exoskeleton. Each module is made up of one or more kinematic chains of the segments and joints. The segments are adjustable not only in length, but also in width, being able to adapt to a wide range of users, according to their physical constitution.

The mechanical structure can be rigid, semi-rigid or flexible, and it can be manufactured in different materials such as metal, fiber, glass, wood, textile, plastic or any variation or combination thereof. Furthermore, it can incorporate one or more casings of rigid, semi-rigid or soft material, made of any material, as decoration or as an insulation system from the surroundings or protector of the exoskeleton, or of the user. The structure can incorporate, in addition to, or instead of the casings a superficial treatment, such as paint, corrosion inhibitor, antioxidant, etc.

The mechanical structure, made up of segments and joints, as commented previously comprises an abduction/adduction joint at the hip, adjustable by means of an actuator controlled by a joint control system that allows for obtaining a range of cervical diaphysiary angles within the desired ranges for patients with anti-physiological gait, due to anatomical anomalies, such as are hips with abnormal cervical diaphysiary angles.

The mechanical structure further comprises a condylar fitting mechanism that allows for passively fitting the condylar angle formed between the femur and tibia in order to adapt it to users with anatomical anomalies such as bow-leggedness or knock-knees.

As described previously, the joints joining the segments of the mechanical structure allow relative movement between two or more successive segments through active, resistive, passive elements or a combination thereof. These joints may be coaxial to the joints of the user or not, and their number may coincide or not with the number of degrees of movement of the human joints. In any case, their purpose is moving the user's joints lending them a natural gait. To do so, and according to recommendations of medical specialists, the following degrees of movement are fundamental:

Flexion and extension of the hip by means of rotation in the sagittal plane.
Abduction adduction of the hip by means of rotation in the lateral plane.
Rotation of the hip by means of rotation in the transverse plane.
Flexion and extension of the knee by means of rotation in the sagittal plane.
Flexion and extension of the ankle by means of rotation in the sagittal plane.
Eversion and inversion of the ankle by means of rotation in the lateral plane.

These 6 degrees of movement in each leg or lower limb are an essential requirement in order to be able to generate a natural and physiologically healthy gait in the user. In the exoskeleton of the present invention, these 6 degrees of movement per leg are actuated. This can be single-joint or multi-joint actuation, in other words n motors can be used to move m joints, wherein n may be greater than, equal to or less than m. For its implementation, any multi-joint transmission system is used: bar mechanisms, belts, cables, pulleys, etc.

The actuation of the main 6 degrees of movement is fundamental in order to be able to guarantee the control of the stable equilibrium of the exoskeleton-user assembly. Furthermore, two of these joints require a special treatment for their biomechanical function: both the knee and the ankle in the sagittal plane:

The knee joint of the present invention comprises an eccentric shaft with respect to the crossing of the upper and lower segments, which allows a flexion greater than 100°, required for sitting, and provides greater stability in the support.

The ankle joint in the sagittal plane comprises an actuator separate from the ankle of the user to reduce the moment of inertia of the leg since the maximum power required in the ankle is approximately 500 W for a subject weighing 70 kg and this would require an actuator of equivalent power, which located at the ankle would cause an increase in weight, volume and moment of inertia that are not desired for an exoskeleton. Instead, the solution proposed by the actuator transmits the movement to the ankle through a bar mechanism and an elastic element that exerts traction on the bars of the bar mechanism, in order to achieve the power requirement without increasing the weight and volume of the actuator, thus constantly contributing to the plantar flexion of the ankle.

The joints that join the segments of the mechanical structure of the exoskeleton of the present invention comprise a joint range adjustable and adaptable to the joint range of the user. This regulation can be mechanical, electronic, programmed or automatic, or any combination thereof.

The mechanical structure comprises an actuation system made up of actuators that confer movement to the joints that can be linear, rotational or any combination of both. Its operating principle can be hydraulic, pneumatic, electric, magnetic, thermal or a combination thereof. They can also be intelligent materials, like ionic polymers, elastomers, piezoelectric materials, etc., or a hybrid system between conventional systems and intelligent materials. These elements can be placed in the mechanical structure of the exoskeleton near the human joints or in any other position as appropriate by functionality criteria. The movement, force or torque is transmitted from the actuators to the joints by means of one or more transmission systems such as gears, belts, cables, pulleys, spindles or direct transmission.

The exoskeleton comprises a fastening system that allows it to carry out its coupling to the human body from the front portion of the body, enabling its positioning from a sitting or a horizontal position without requiring a functional transfer, wherein the fastening system is adjustable and adaptable to the anatomy of the user and has adjustable tension.

The fastening system comprises a rigid lumbar reinforcement that in turn comprises two or more segments that are able to be coupled, two of which are joined to the segments of the exoskeleton by means of one or more rotation shafts, the lumbar reinforcement being retractable by means of successive rotations until it is located in the sagittal plane in order to allow positioning the exoskeleton from the front of the user. Once the exoskeleton is coupled to the user, the segments that make up the lumbar reinforcement are turned back again until they reach their functional lumbar position, securing all the segments to each other by means of any coupling system.

This positioning method exploits the modularity of the design of the exoskeleton, each of the limbs being able to be placed independently and finally joining through the lumbar reinforcement.

The fastening system further comprises an ischiatic support, the function of which is to transfer the user's weight to the exoskeleton, wherein the ischiatic support is preferably a girth located under the buttocks of the user, which supports a part or all of the user's weight and transmits it to the mechanical structure. The ischiatic support is adjustable, and the tension thereof can be adjusted through a tensioning mechanism that can be manual or automatic, apart from being removable, which results in the easy placement of the exoskeleton.

The fastening system further comprises fastening devices for securing the exoskeleton to the legs of the user, not being rigid in their back portion in order not to obstruct the positioning of the exoskeleton on the human body from the front of the body.

The fastening system further comprises a device for anchoring to the shoe of the user.

The exoskeleton comprises an on board power system that provides energy to the actuation system and to a computer system. The on board power system can be made up of batteries, fuel cells, alternating current generators, hydraulic system, electro-hydraulic system, piezo-hydraulic system, pneumatic system, piezo-pneumatic system, or any combination of these systems. The on board power system can be modular, so that each of the modules that make up the exoskeleton is powered independently. Thus, an exoskeleton made up of two lower limbs can include at least two power modules, placed in the lateral portion of the limbs, so as not obstruct the user in supporting their back or lying down while at the same time it can be easily accessed for replacement or recharge.

The exoskeleton comprises a sensory system that monitors the movement of the exoskeleton, which depends on the state of the exoskeleton itself, on the user, on the interaction of the user with the exoskeleton and the surroundings in each moment. This system comprises:
  a. A proprioceptive subsystem that instantly determines the state of the robot,
  b. A physiological subsystem, which determines the state of the user by means of biomarkers,
  c. An exteroceptive subsystem, which determines the state of the surroundings instantly or over a period of time,
  d. A perceptive subsystem for the exoskeleton-user-surroundings interaction, which determines the state of the mutual interaction between the three previous subsystems, and is able to include all, some or any combination of these subsystems. To do so, the sensory system consists of combinations of sensory elements of a physical, mechanical, chemical or biological nature, such as force, torque, pressure, position, or speed sensors, lasers, cameras, goniometers, electromyographic sensors, ocular activity sensors, brain activity sensors, cardiac and respiratory frequency gauges, and spirometer among other options.

The exoskeleton comprises a movement control system that receives information from the sensory system, and which is composed of one or more of the following subsystems:
  a. Joint control system.
  b. Limb control system.
  c. Control system of the center of mass of the exoskeleton-user assembly.

The exoskeleton further comprises a user interface system that interprets the movement intention of the user and transmits this information to the movement control system. This user interface system can be made up of a joystick, tablet, mobile phone, touch screen, keyboard, mouse, microphone, camera, eye-movement reader, electromyography sensors (EMG), brain-computer interfaces (BCI), electrooculography interfaces (EOG), force or torque sensors, pressure sensors, inertial measurement units (IMU), position, speed or inclination sensors, etc., or any combination of these devices, and includes the electronics and the information processing required for the interface to capture the movement intention of the user.

The exoskeleton comprises one or more on board processing units that carry out all the computational processing of one or more of the sensory, user movement control and interface systems. The processing units can be based on any type of processor, microprocessor, field-programmable gate array (FPGA) or any combination thereof.

BRIEF DESCRIPTION OF THE DRAWINGS

As a complement to the description provided herein, and for the purpose of helping to make the characteristics of the invention more readily understandable, a set of drawings is attached as an integral part of the description, which, by way of illustration and not limitation represent the following:

FIG. 7a.—Shows a detailed view of the anchoring of the exoskeleton to the shoes.

FIG. 7b.—Shows a detail of the bar mechanism and elastic element that complements the ankle joint actuator.

DETAILED DESCRIPTION OF THE INVENTION

The exoskeleton for assisting human movement of the present invention is described in a detailed manner below.

The exoskeleton comprises a modular mechanical structure comprising segments joined by joints. The mechanical structure comprises an abduction/adduction joint at the hip (32), adjustable by means of an actuator (42) that allows for obtaining a range of cervical diaphysiary angles within the desired ranges for patients with anti-physiological gait, due to anatomical anomalies, such as hips with abnormal cervical diaphysiary angles.

Figure 10A:
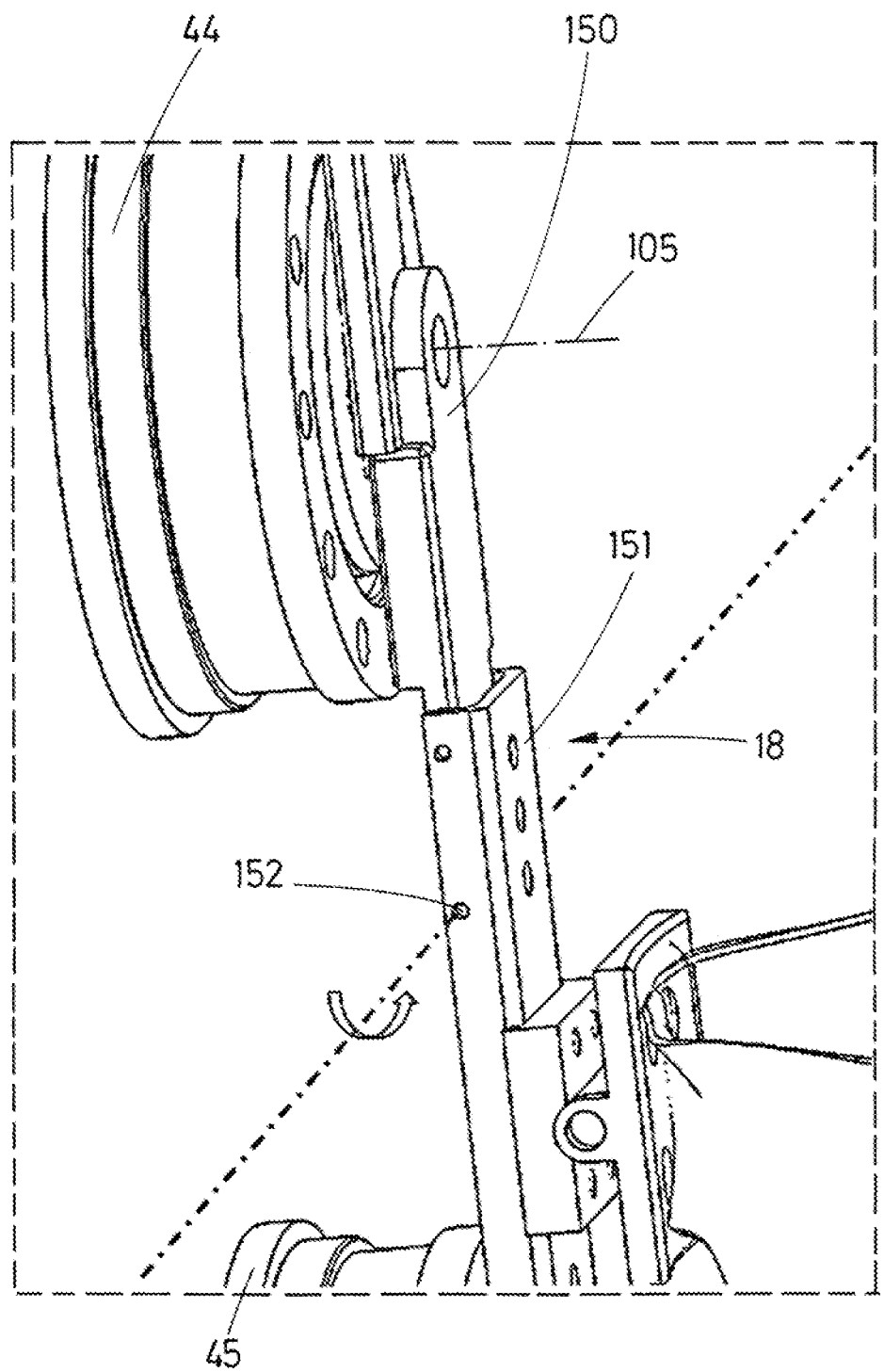
FIGS. 10a and 10b.—Show the mechanical structure adapted to normal and abnormal anatomy, with a detail of the condylar fitting mechanism in different positions.
Figure 10B:
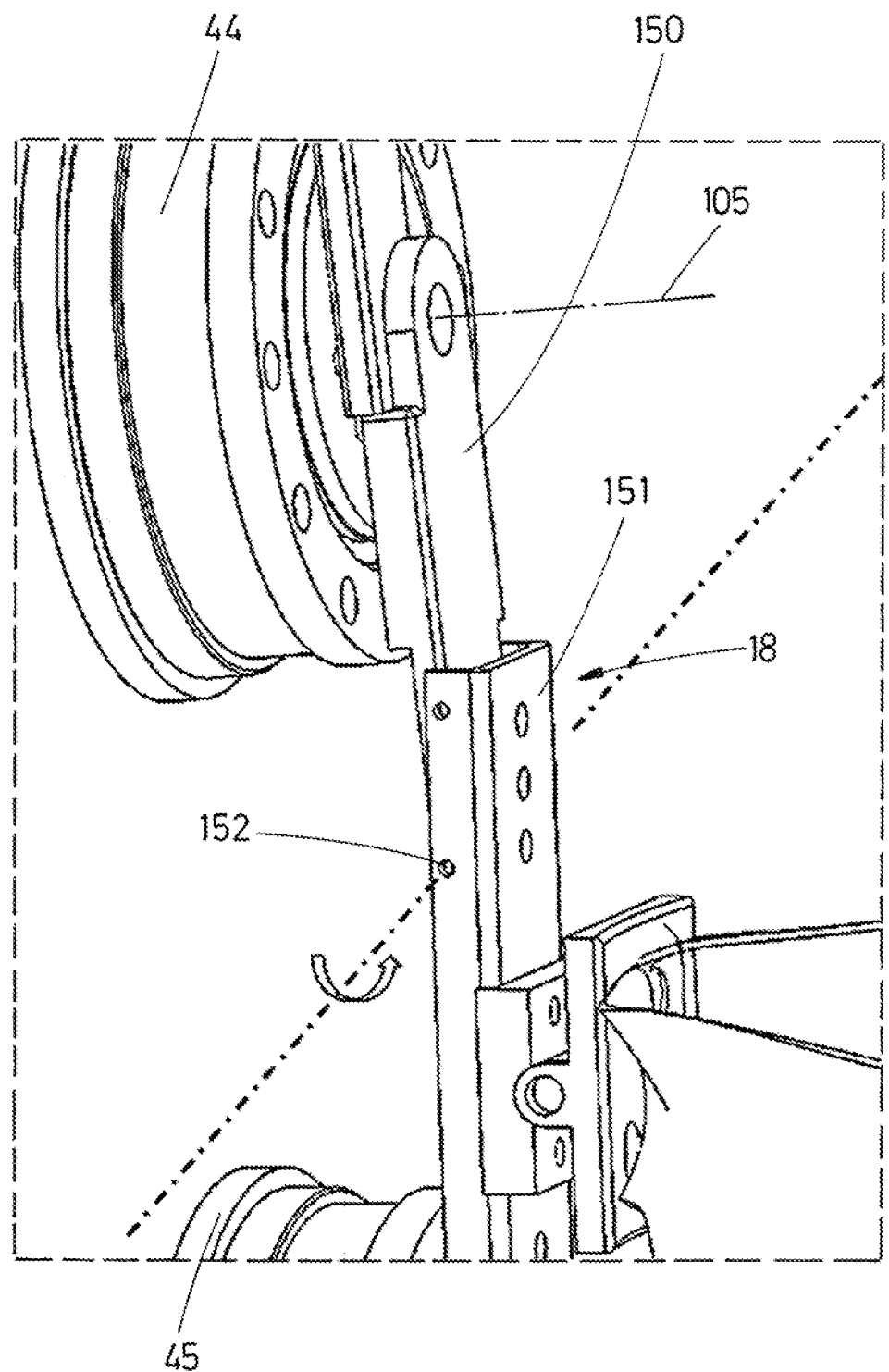

The mechanical structure further comprises a condylar fitting mechanism (18) that allows for passively fitting the condylar angle formed between the femur and tibia in order to adapt it to users with anatomical anomalies such as bow-leggedness or knock-knees. FIGS. 10a and 10b show a first exemplary embodiment of the condylar fitting mechanism (18) comprising a proximal segment (150) adjacent to a knee joint (105) and a distal segment (151) further away from the knee joint, wherein the proximal segment (150) is shorter and is introduced into the distal segment (151), and wherein both segments (150, 151) are joined by means of a pin (152) arranged in perpendicular direction to the tibia of the user and in the advance direction, wherein the adjustment of the condylar angle is carried out by means of a threaded mechanism arranged in the lower end of the distal segment. FIG. 10 shows the mechanical structure of the exoskeleton for a user without anomalies and FIG. 10b shows the mechanical structure fitted for a user with coxa vara and genu valgum.

The exoskeleton comprises 6 degrees of movement in each leg, which are actuated. These degrees of movement are the following:

Flexion and extension of the hip (31) by means of rotation in the sagittal plane;
Abduction-adduction of the hip (32) by means of rotation in the lateral plane;
Rotation of the hip (33) by means of rotation in the transverse plane;
Flexion and extension of the knee (34) by means of rotation in the sagittal plane;
Flexion and extension of the ankle (35) by means of rotation in the sagittal plane;
Eversion and inversion of the ankle (36) by means of rotation in the lateral plane;
each actuated by means of an actuator (41, 42, 43, 44, 45, 46) respectively.

Figure 1A:
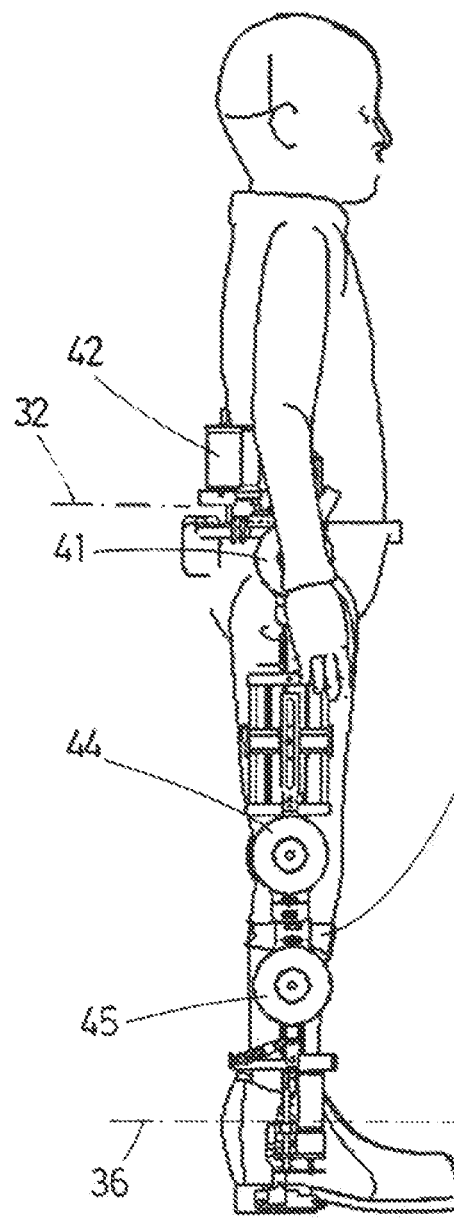
FIGS. 1a to 1c.—Show an embodiment of a lower limb exoskeleton with a user, in three views: profile, front and perspective, respectively. They indicate the elements of the fastening system of the user to the exoskeleton.
Figure 1B:
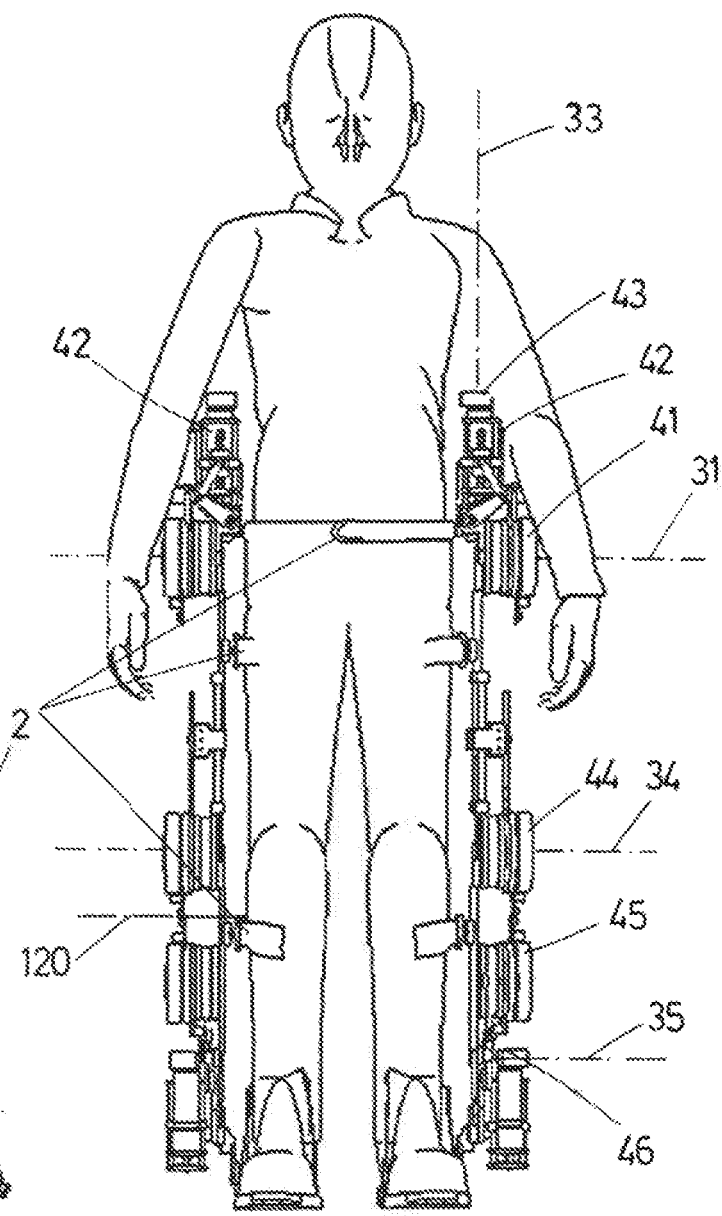
Figure 1C:
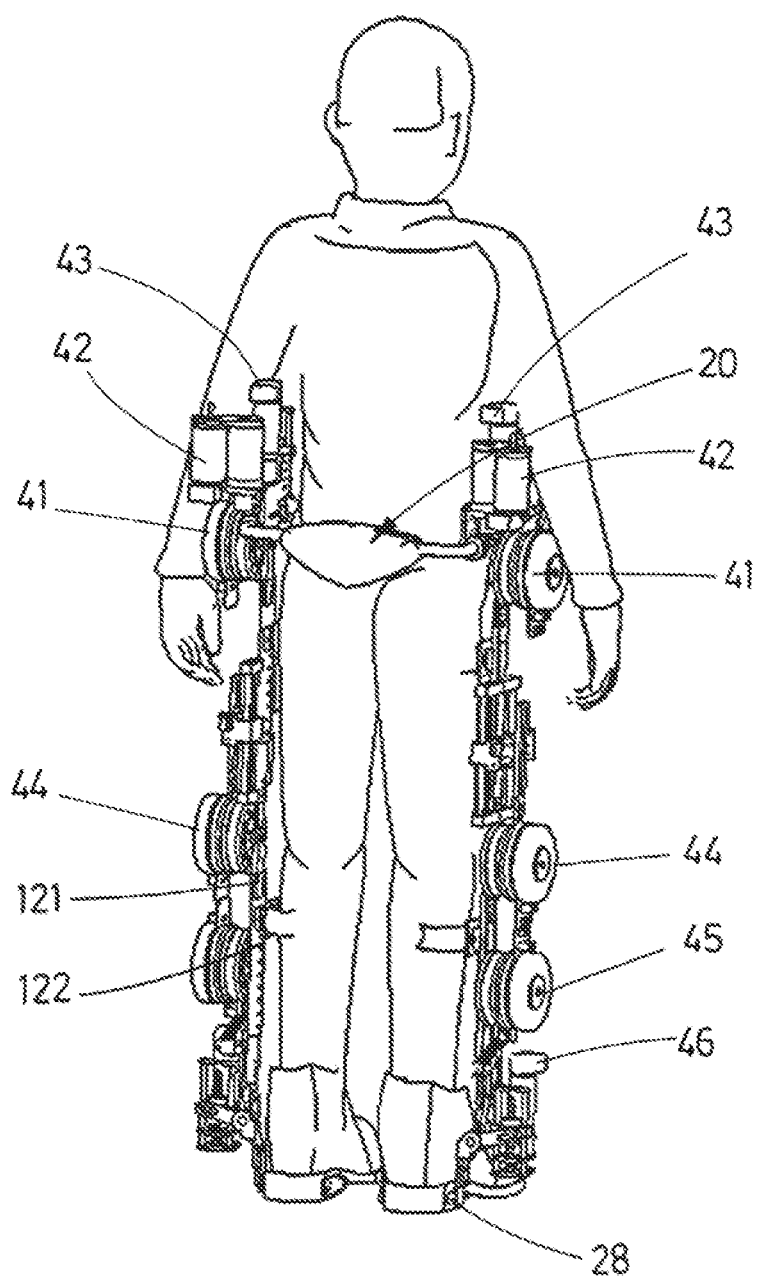

The degree of movement for carrying out flexion and extension of the knee (34) by means of rotation in the sagittal plane is defined because the mechanical structure comprises a shaft (120) that is eccentric with respect to the crossing of an upper segment (121) and a lower segment (122) eccentric shaft (120) actuated by the corresponding actuator (44), which allows a flexion above 100°, required for sitting, and provides greater stability in the support, as shown in FIG. 1.

Figure 11A:
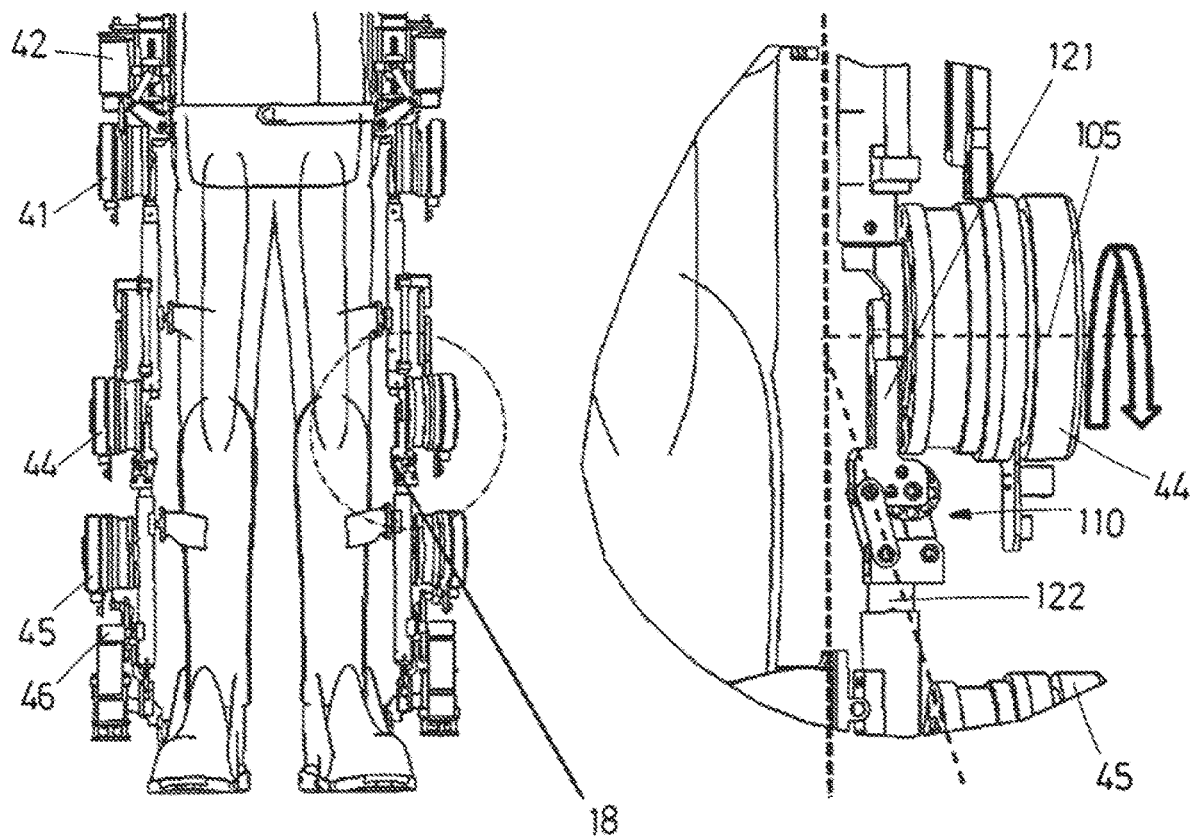
FIGS. 11a and 11b.—Show a variant of the invention for the adjusting the condylar angle, making use of a four bar mechanism in different positions.
Figure 11B:
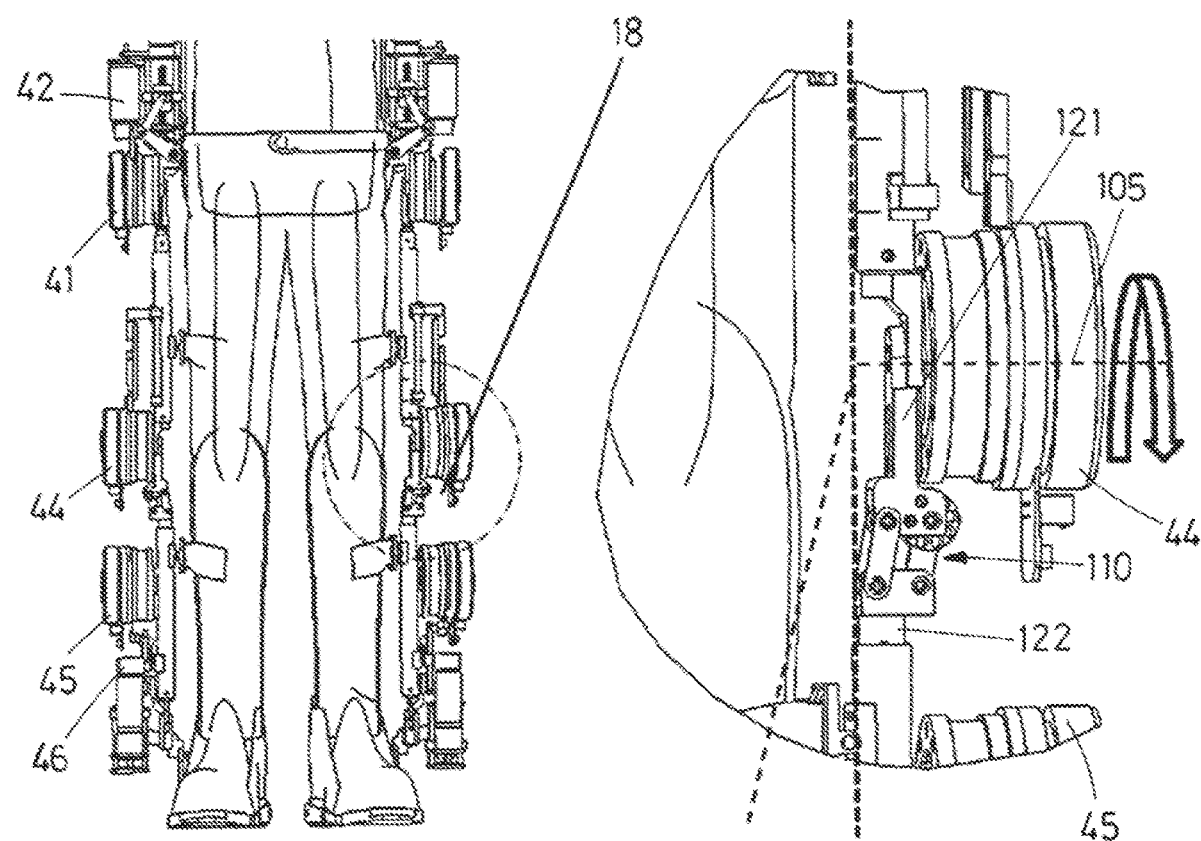

FIGS. 11a and 11b show a second exemplary embodiment, wherein the condylar fitting mechanism (18) comprises a four-bar mechanism (110) arranged under the knee joint (105). In this way the upper segment (121) is shifted, although it is kept parallel to the inner segment (122), varying the condylar angle and fitting it to the user.

The degree of movement for carrying out the flexion and extension of the ankle (35) by rotation in the sagittal plane comprises an actuator (45) separate from the ankle of the user that transmits the movement to the ankle through a bar mechanism (47) and an elastic element (48) that exerts traction on the bars of the bar mechanism (47), wherein the effect of the elastic element is to constantly contribute to the plantar flexion of the ankle. The combined operation of the actuator (45) and elastic element (48) is as follows: during the support, the user's weight and the action of the actuator (45) overcome the counter-torque generated by the elastic element (48) and the phase is executed normally. Upon reaching the lift-off phase, the effect of the user's weight disappears, while the actions of the elastic element (48) and actuator (45) combine in favor of the plantar flexion, which generates the instantaneous power required for the impulse. During the foot transfer phase, the actuator (45) has enough power to counteract the effect of the elastic element (48) and generate the dorsal flexion of the ankle to prevent impact with the ground. FIG. 7b details an implementation of the ankle joint and its position during the support phase and during the impulse.

The exoskeleton comprises a fastening system (2) that allows it to carry out its coupling to the human body from the front of the body, allowing its positioning from a sitting or lying position without requiring a functional transfer.

Figure 4A:
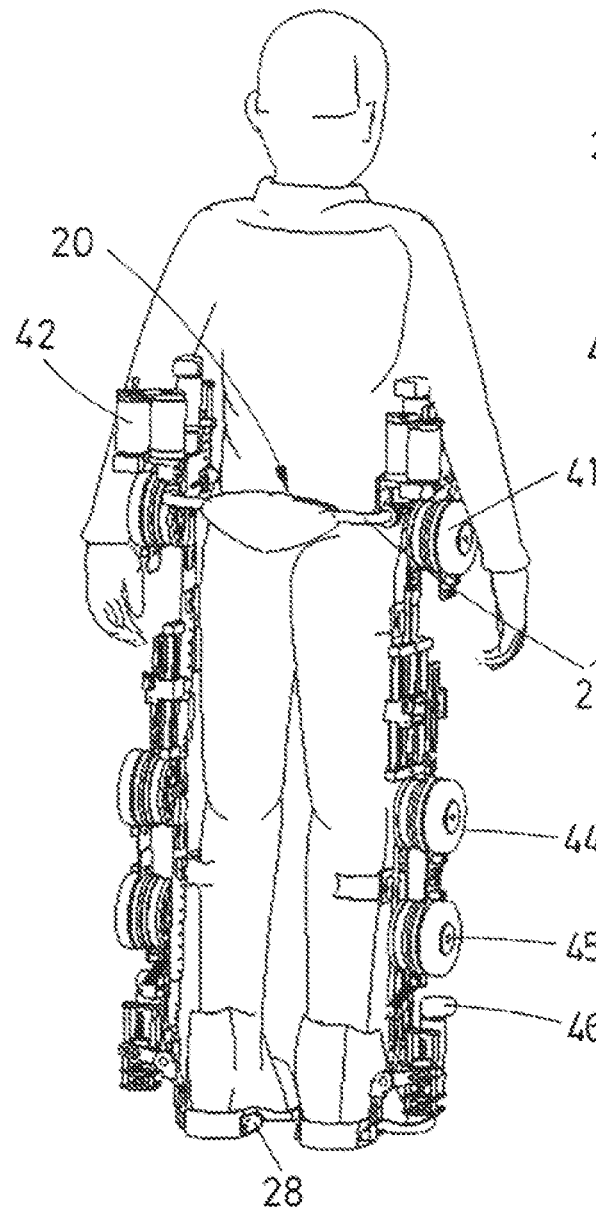
Figure 4B:
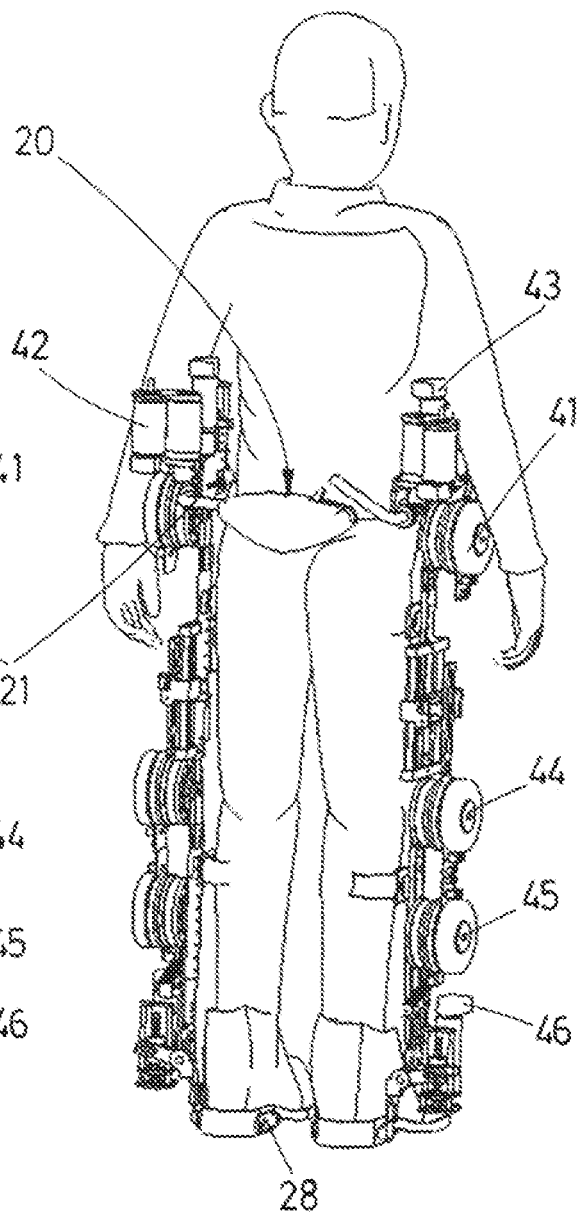
Figure 4C:
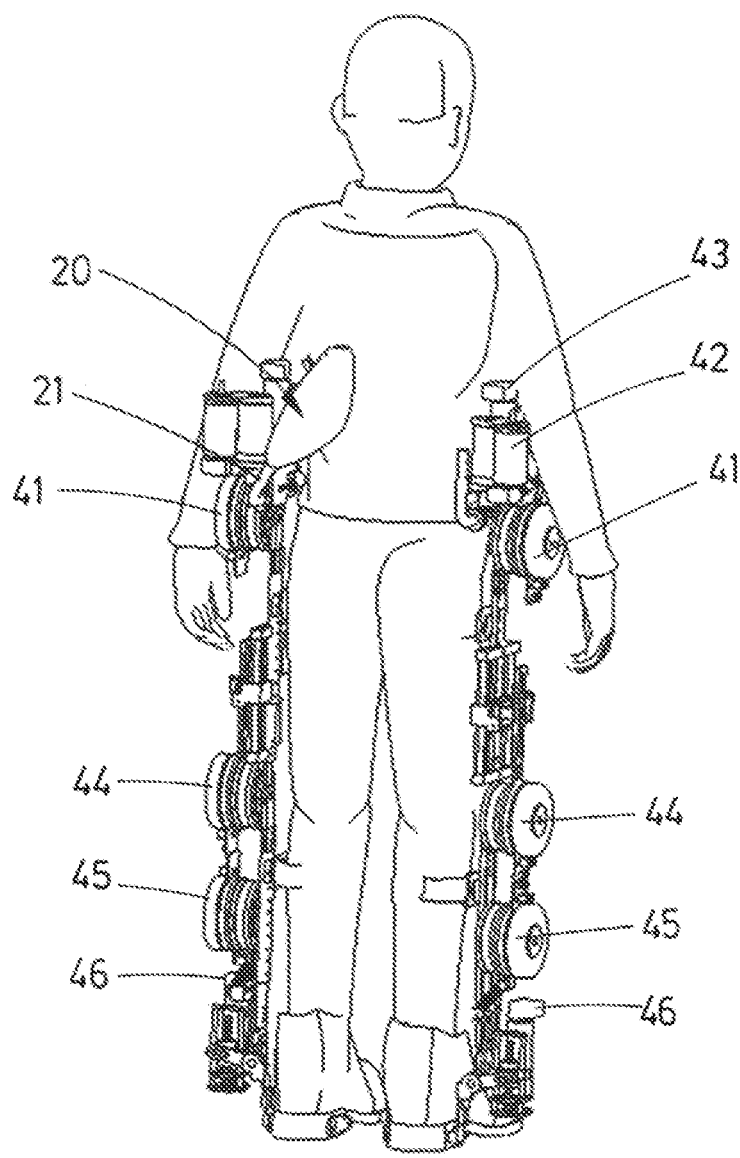
Figure 5:
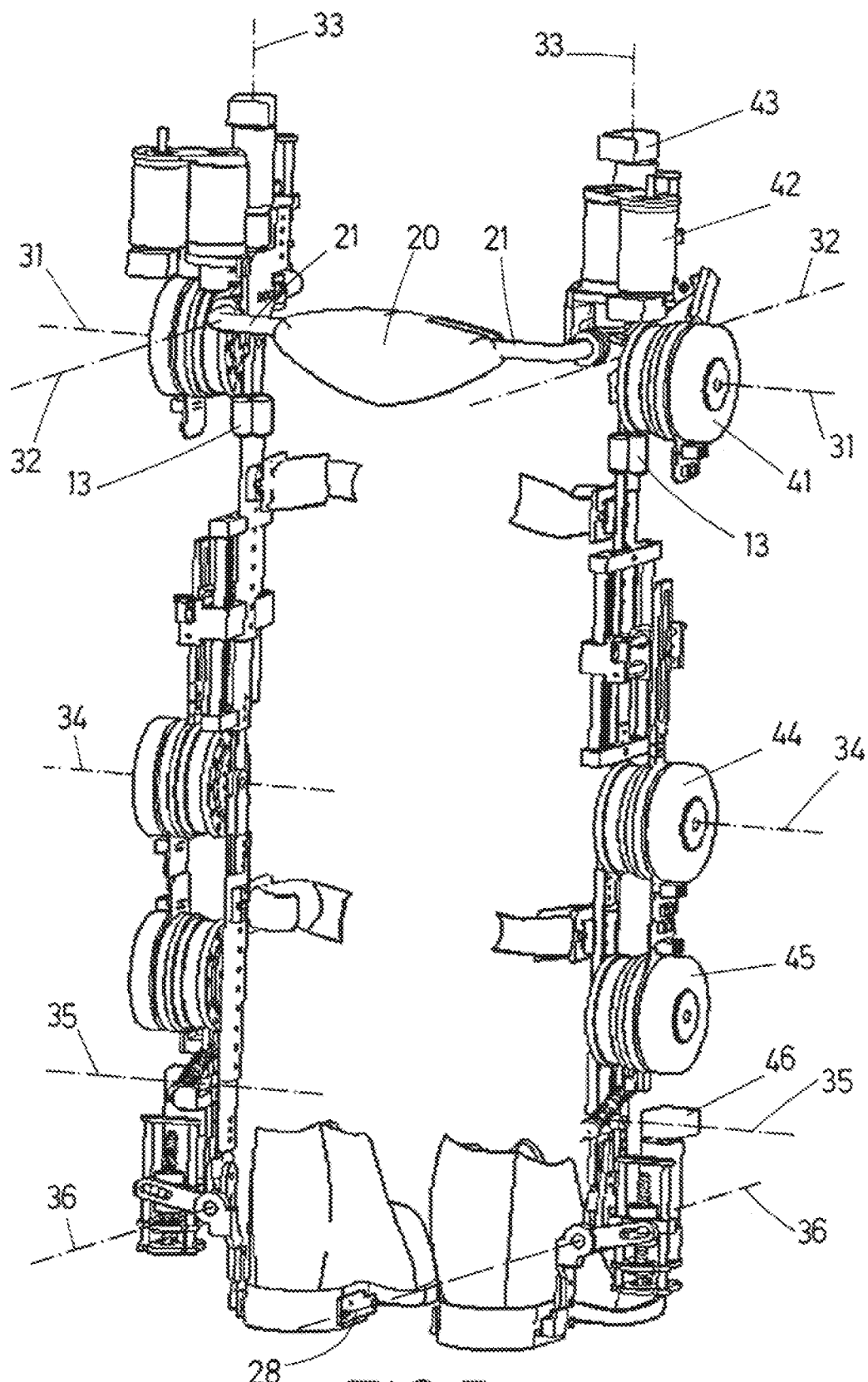
FIG. 5.—Shows the degrees of joint movement and the corresponding actuators for an embodiment of a lower limb exoskeleton of 6 degrees of freedom per leg.

The fastening system (2) comprises a rigid lumbar reinforcement (20) that in turn comprises two or more segments (21) that are able be coupled, as shown in FIGS. 3a to 3d, two of which are joined to the segments of the exoskeleton by means of one or more rotation shafts (22), wherein the rigid lumbar reinforcement (20) is retracted by means of successive rotations until it is located in the sagittal plane in order to allow positioning the exoskeleton from the front of the user. Once the exoskeleton is coupled to the user, the segments that make up the rigid lumbar reinforcement (20) are turned back again until they reach their functional lumbar position, the segments being secured to each other by means of a coupling system (23). FIGS. 4a to 4c show a view of the rigid lumbar reinforcement (20) in two different positions: FIG. 4a shows the natural operating position of the lumbar reinforcement (20), in which both segments (21) that are able to be coupled are connected and occupy the rear portion of the exoskeleton. FIGS. 4b and 4c show the retraction sequence until both segments (21) that are able to be coupled are completely stowed parallel to the sagittal plane, leaving the inner space completely free inside the exoskeleton in order to proceed to its positioning from the front of the user.

This positioning method exploits the modularity of the design of the exoskeleton, each of the limbs being able to be placed independently and finally joining through the lumbar reinforcement (20) and the rest of the components of the fastening system (2).

Figure 2:
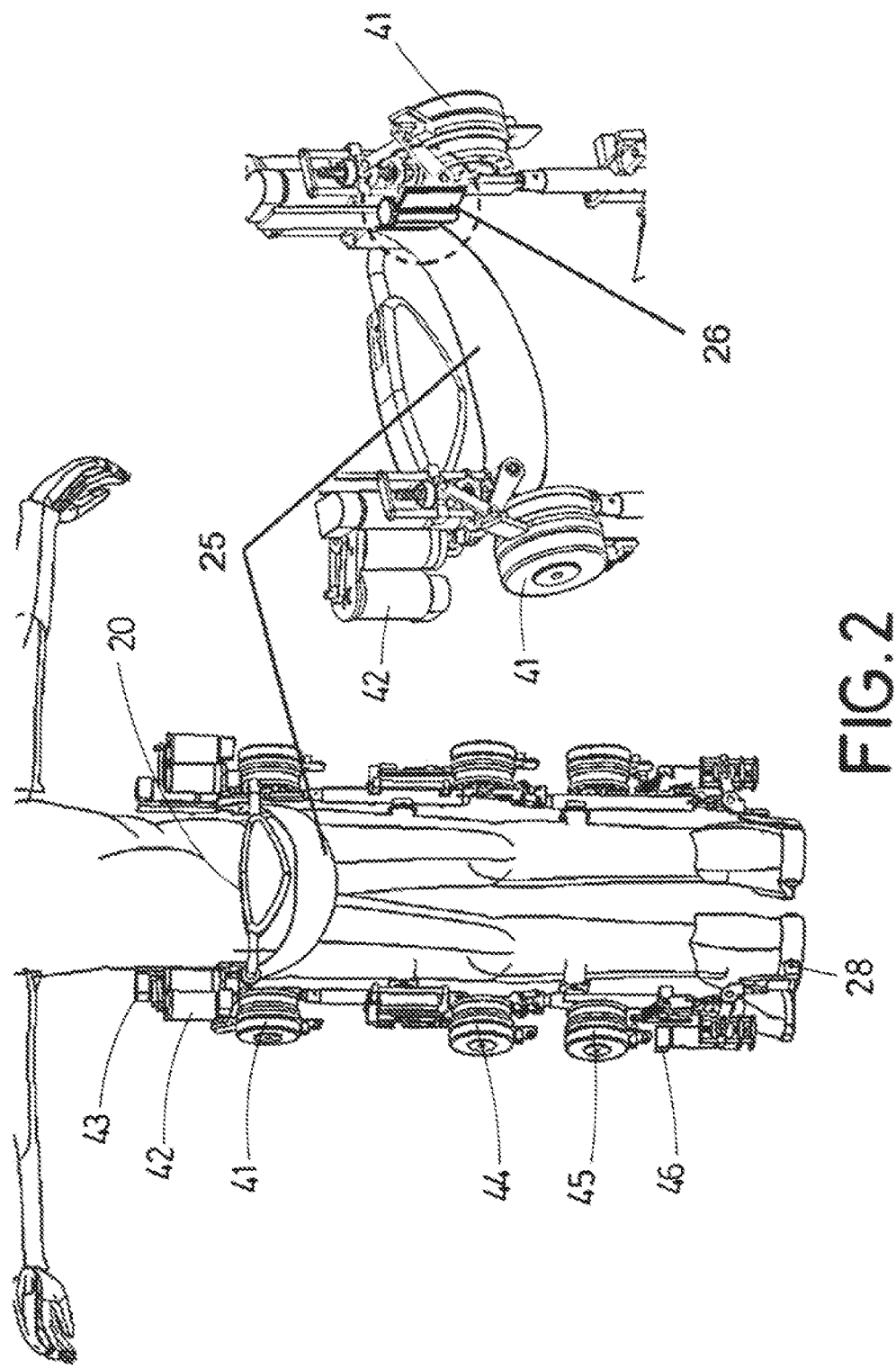
FIG. 2.—Shows the ischiatic support in the view on the left, and a manual adjustment system for the same in the detail on the right.
Figure 3A:
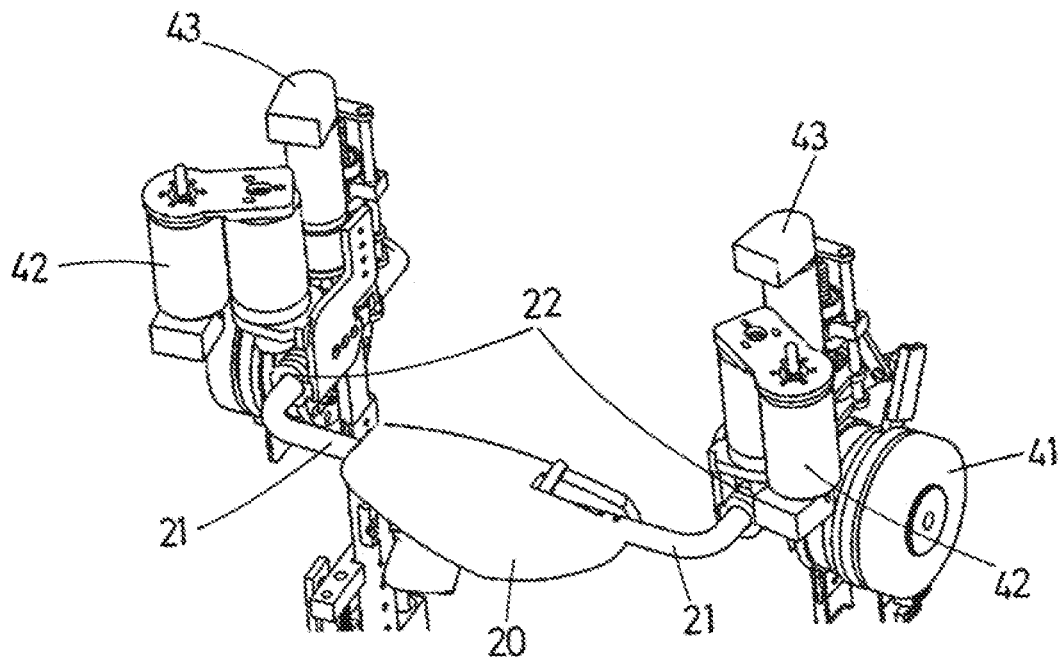
FIGS. 3a to 3d and 4a to 4c.—Show in detailed view of the retraction process of the rigid lumbar reinforcement.
Figure 3B:
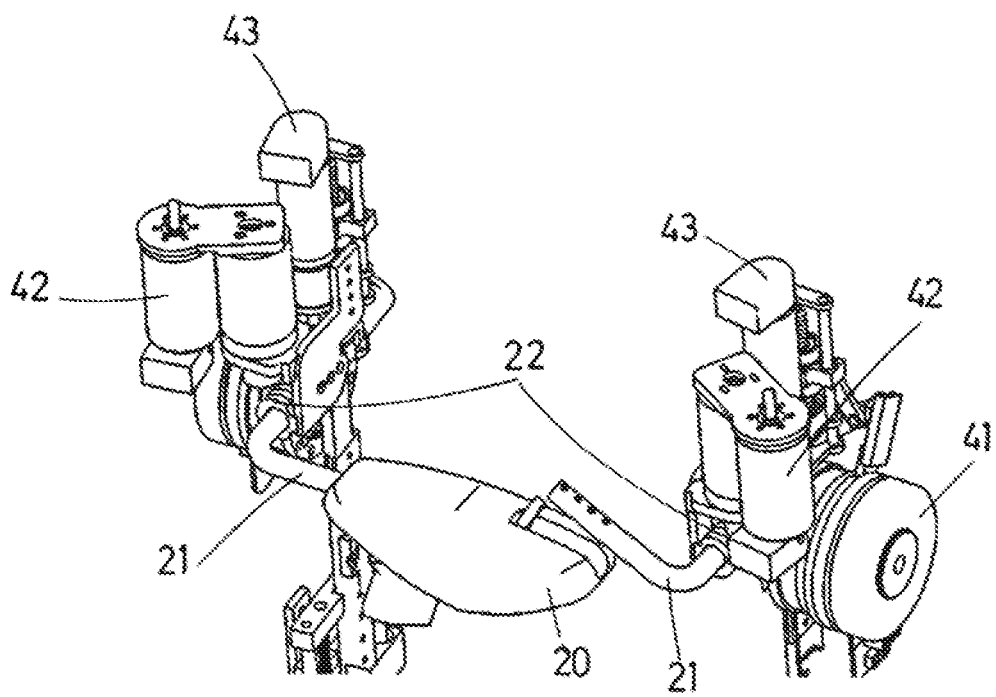
Figure 3C:
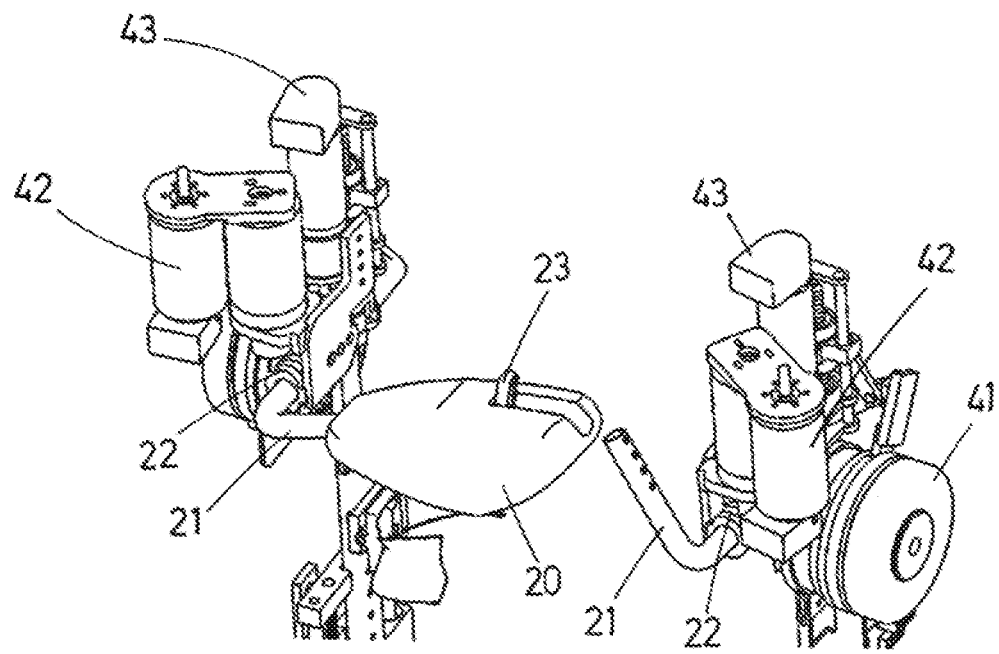
Figure 3D:
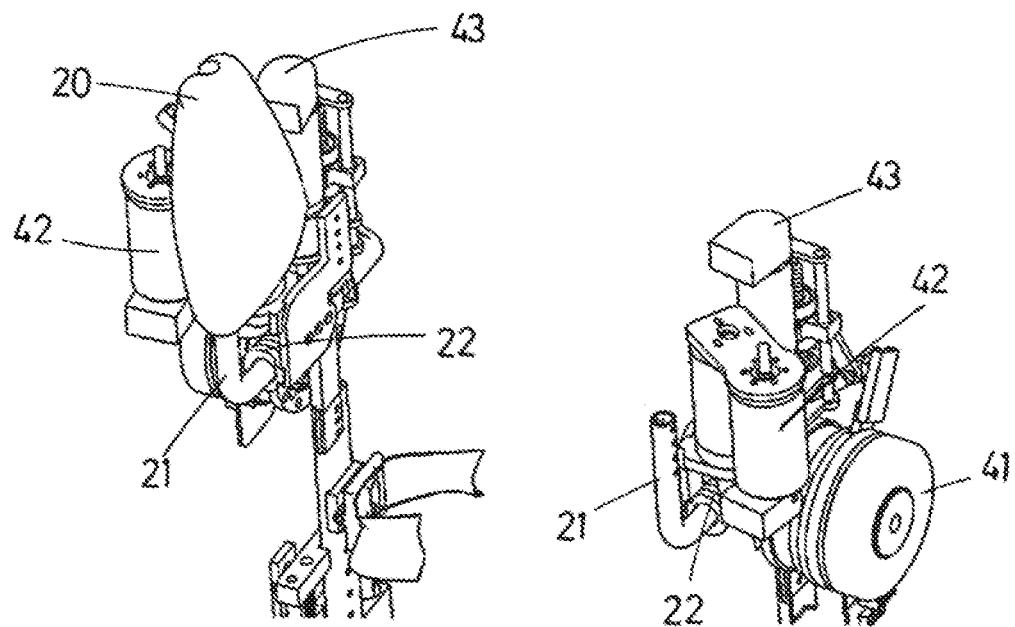

The fastening system (2) further comprises an ischiatic support (25) the function of which is to transfer the user's weight to the exoskeleton, wherein the ischiatic support is preferably a girth located under the buttocks of the user, which supports a part or all of the user's weight and transmits it to the mechanical structure, as seen in FIG. 2. The ischiatic support (25) is adjustable, the tension thereof being can be adjusted through a tensioning mechanism (26) that can be manual or automatic, apart from being removable, which results in the easy placement of the exoskeleton. In order to not obstruct the positioning of the exoskeleton, the ischiatic support (25) can buckle and unbuckle, depending on the positioning method of the exoskeleton.

The ischiatic support (25) can also be carried out by means of thermoplastic thigh pieces, especially in those patients with low bone density like osteoporosis.

The fastening system (2) further comprises fastening devices for securing the exoskeleton to the legs of the user, not being rigid in their back portion in order not to obstruct the positioning of the exoskeleton on the human body from the front of the body.

The fastening system further comprises a device for anchoring (28) to the shoe of the user, which is carried out permanently, by means of rivets or another fastening system, or detachably by means of screws or other fitting means, on the inside of the shoe or on the outside. Since most patients need to use orthopedic footwear, the use of exoskeletons with a sole to which the user's shoe is fitted is not recommended; it is preferable that the mechanical structure be anchored directly over the natural sole of the footwear, so as to not interfere with the pathology of the foot. FIGS. 7a and 7b show an exemplary embodiment of the anchoring of the exoskeleton to the shoe of the user, wherein brace-type fastening is used on the heel of the sole and is clamped by means of screws or rivets (28).

The exoskeleton comprises an on board power system (13) that provides energy to an actuation system made up of the actuators (41, 42, 43, 44, 45, 46) comprising the mechanical structure and a computer system (14).

The exoskeleton further comprises an on board sensory system (3) that monitors the movement of the exoskeleton and comprises:
 e. A proprioceptive subsystem (4) that instantly determines the state of the robot,
 f. A physiological subsystem (5), which determines the state of the user by means of biomarkers,
 g. An exteroceptive subsystem (6), which determines the state of the surroundings instantly or over a period of time,
 h. A perceptive subsystem (7) for the exoskeleton-user-surroundings interaction, which determines the state of the mutual interaction between the three previous subsystems (4, 5, 6),
being able to include all, some or any combination of these subsystems (4, 5, 6, 7).

The exoskeleton comprises a movement control system (12) that receives the information from the on board sensory system (3), and which is composed of one or more of the following subsystems:
 a. Joint control system (8).
 b. Limb control system (10).
 c. Control system of the center of mass of the exoskeleton-user assembly (11).

The joint control system (8) guarantees the desired joint movement in the user based on the tracking of a reference signal that can be any physical, mechanical or biomechanical magnitude such as joint position, speed, force, torque or any derivative or combination thereof, by means of an automatic control technique (Proportional, Integral, Derivative, neuronal control, diffuse control, heuristic control, non-linear control, robust control, optimal control, etc., or any combination thereof).

Figure 6A:
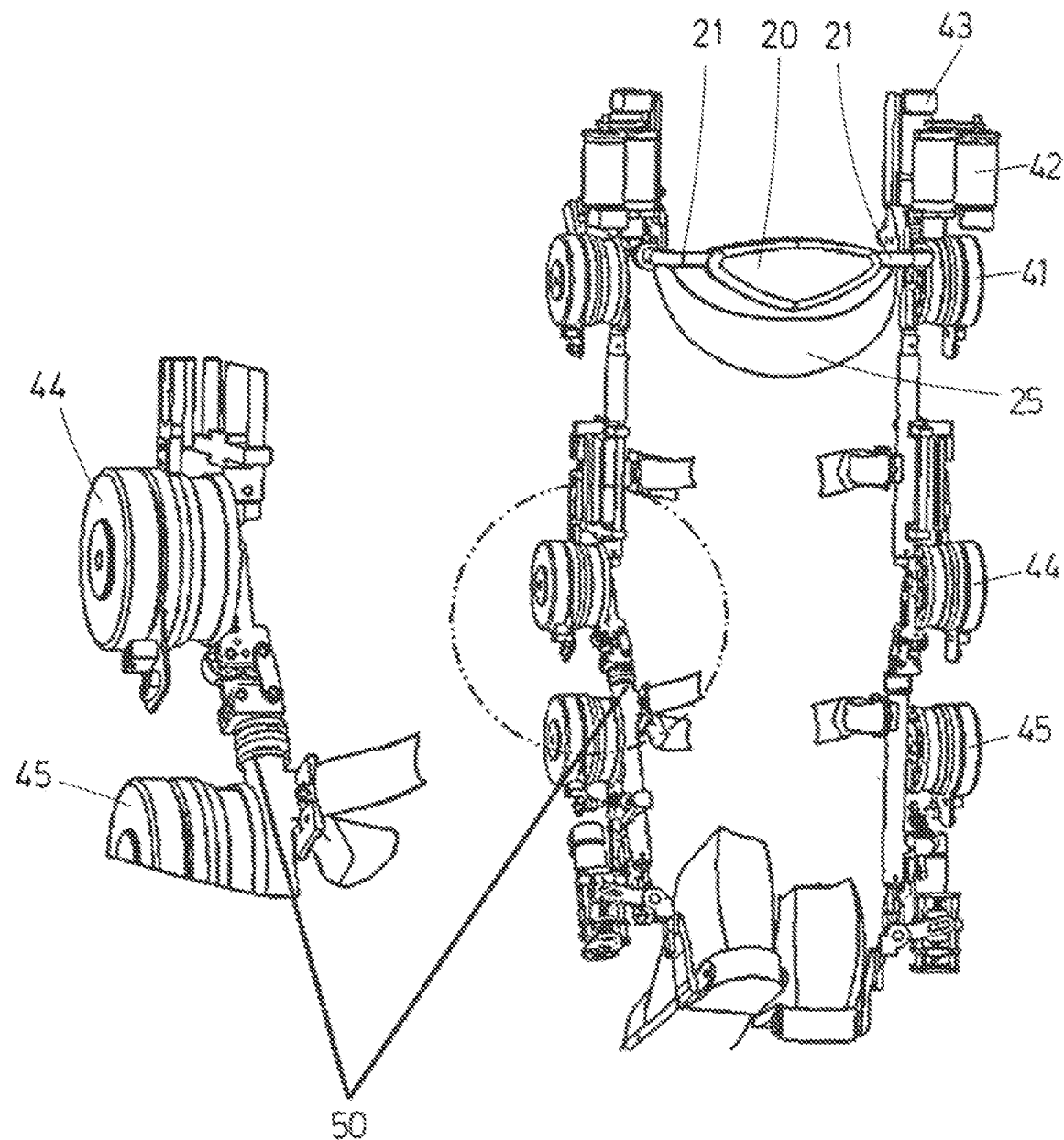
FIGS. 6a and 6b.—Show a variant of the invention with an extra degree of freedom that enables rotation of the knee in several positions.
Figure 6B:
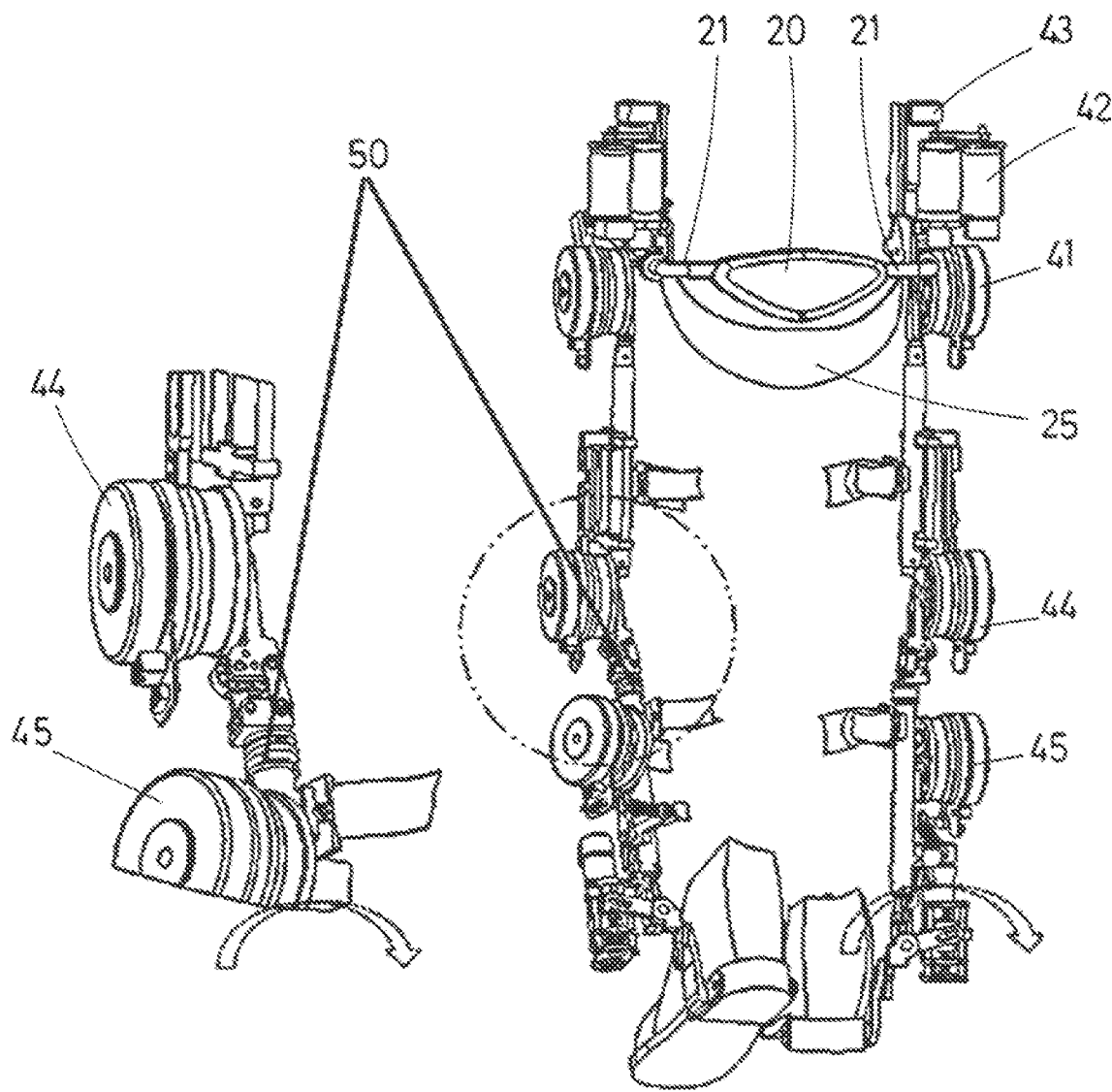
Figure 8:
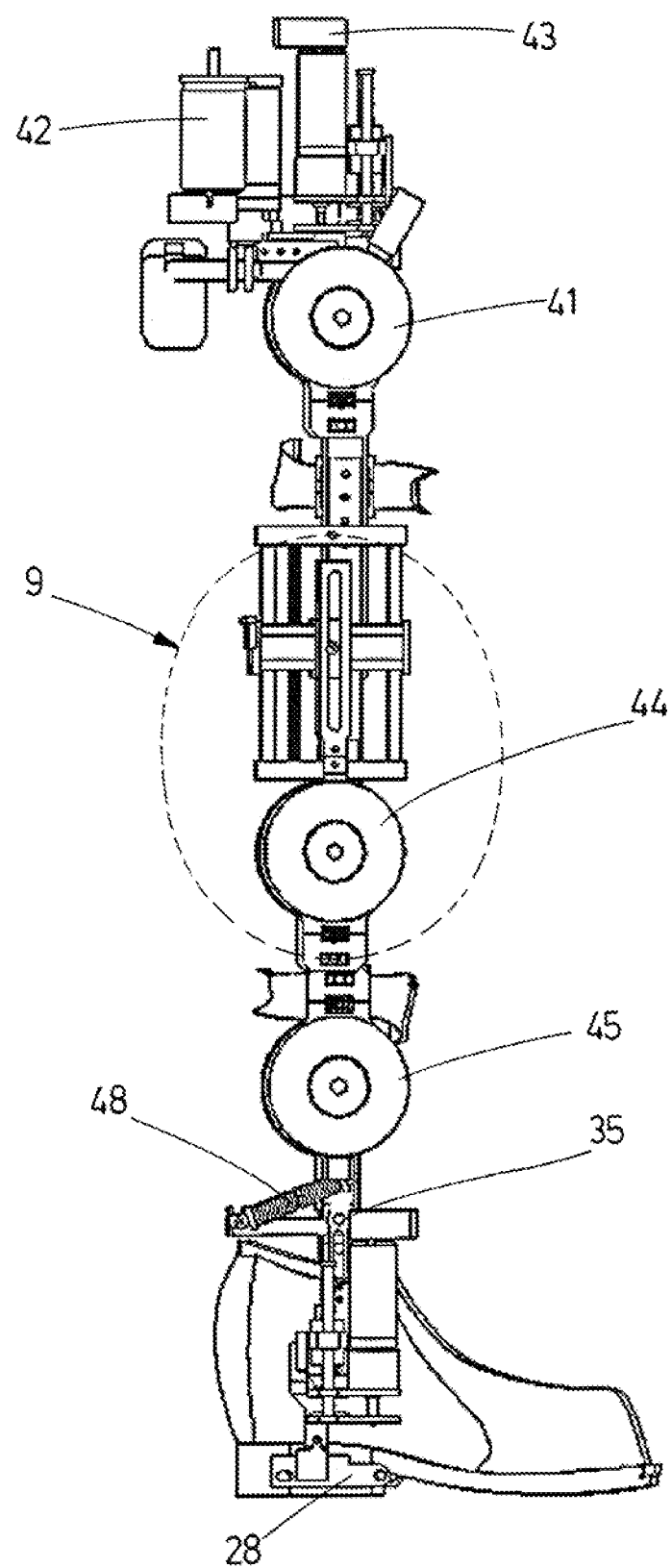
FIG. 8.—Shows a lateral view of a lower limb exoskeleton and indicates a variable and controllable impedance actuator at the knee.

Given that most exoskeleton users have spasticity, spasms and other anomalies, it is necessary to adapt the joint movement to those effects in order to avoid damaging the tendinomuscular tissue of the user. To do so, the joint control system (8) incorporates an impedance control module that receives information from the sensory system (3) and in particular from the physiological subsystem (5) and automatically adapts the movement of the joint of the exoskeleton to the range, rigidity and spasticity of the equivalent joint of the user. In some embodiments of the invention, this impedance control module can be implemented by means of a variable and controllable impedance joint, as described in the application for Spanish patent P201330882 included herein as a reference, which has important advantages as compared to programmed modules. FIGS. 6a and 6b show an embodiment of the invention that incorporates a variable and controllable impedance joint (50) in the knee.

The movement control system of each lower limb (10) synchronizes the joint control systems (8) that integrate the kinematic chain corresponding to that limb depending on the time, position and/or time derivatives thereof, and/or force and/or torque and/or time derivatives thereof, and/or depending on the information from the sensory system in order to automatically adapt the movement of the lower limb (10) to the rigidity conditions of the surroundings in contact.

The movement control system of the center of mass (11) of the exoskeleton-user assembly synchronizes the control systems of each lower limb (10) depending on the time and/or position and/or derivatives thereof and/or force and/or torque and/or derivatives thereof, or any other physical, mechanical or biomechanical variable and/or through the feedback from the information from the on board sensory system (3) and/or through the information ordered by the user by means of a user interface system (16) and/or following a movement reference pattern based on joint positions and/or derivatives thereof and/or torques and/or joint forces and/or positions of the lower limbs (10) and/or derivatives thereof and/or forces and/or torques in the lower limbs (10) and/or any biomechanical parameter.

Figure 9:
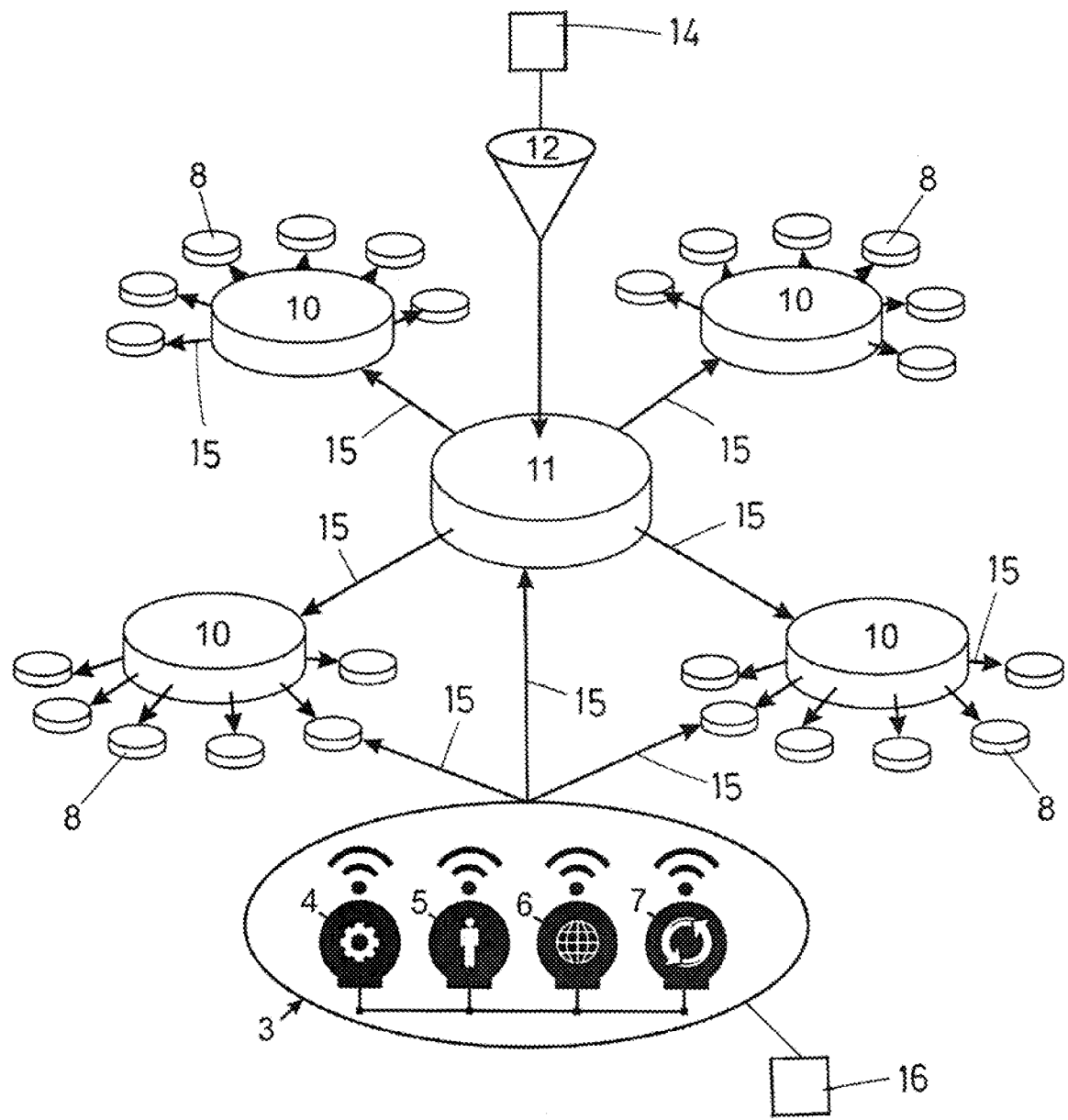
FIG. 9.—Shows a diagram of the control system.

FIG. 9 shows an exemplary embodiment of the movement control system (12) for an exoskeleton with 4 limbs, two arms and two legs, and 6 joints per limb.

The movement control system of the center of mass (11) has the ability to adapt the reference patterns to the biomechanical conditions of the user, by means of an automatic reference pattern adapter. This automatic reference pattern adapter fits the movement patterns to the joint range, muscle strength and instantaneous conditions of each limb of the user.

This movement control system of the center of mass (11) maintains the exoskeleton-user assembly in dynamically or statically stable equilibrium even in the face of slight external disturbances. Equilibrium control is carried out based on the tracking of a desired stability index, which can be based on the nominal trajectory of the Pressure Center or of the Zero Moment Point (ZMP), on the Normalized Dynamic Energy Stability Margin (NDESM), or any other stability index. Based on an instantaneous measuring of the index and comparing it to the desired or par value, the difference between both values is minimized by means of any control technique (proportional, derivative, integral, blurry, neuronal, optimal etc. or any combination thereof) by means of the generation of a movement or a torque in the center of mass of the robot-user assembly or in any of its limbs. The control system of the center of mass (11) will determine if it is necessary to modify the gait pattern in order to maintain equilibrium.

The joint control system (8), the movement control system of each limb (10), and the movement control system of the center of mass (11) can be combined with a human actuation system whereby the muscles of the user participate in a certain degree in the generation of movement. This human actuation system can be carried out directly by means of the voluntary movement of the user, or indirectly by means of functional electrical stimulation (FES) or a combination of both. These control systems can also be combined or synchronized with a central pattern generator (CPG).

The user interface system (16) that interprets the movement intention of the user and transmits this information to the movement control system. This user interface system (16) can be made up of a joystick, tablet, mobile phone, touch screen, keyboard, mouse, microphone, camera, eye-movement reader, electromyography sensors (EMG), brain-computer interfaces (BCI), electrooculography interfaces (EEG), force or torque sensors, pressure sensors, inertial measurement units (IMU), position, speed or inclination sensors, etc., or any combination of these devices, and includes the electronics and the information processing required for the user interface system (16) to capture the movement intention of the user.

The exoskeleton comprises a communication system (15) that acts as a link between the control systems (8, 10, 11), the sensory system (3) and the user interface system (16) or between any combination thereof. This communication can be wired, wireless or any combination of both, by means of any communication protocol (CAN, Ethernet, LAN, etc.).

The exoskeleton further comprises one or more on board processing units that carry out all the computational processing of one or more of the sensory (3), user movement control (8, 10, 11) and user interface (16) systems. The processing units can be based on any type of processor, microprocessor, field-programmable gate array (FPGA) or any combination thereof.

All of the processing electronics, as well as the on board power source of the exoskeleton is placed throughout the mechanical structure. If the power source is based on rechargeable or replaceable batteries, these are located in the lateral and front portion of the exoskeleton in order to facilitate their charging or replacement by the user.

The joints joining the segments of the mechanical structure of the exoskeleton of the present invention comprise a joint range adjustable and adaptable to the joint range of the user. This regulation can be mechanical, electronic, programmed or automatic, or any combination of these.

a. Mechanical: by means of a stop or sliding brake, by means of threading or by means of any other linear displacement system.
  b. Electronic: by means of the use of limit sensors or any similar device that detects the limit joint position and commands stopping the joint motor.
  c. Programmed: the user or another responsible person (a medical professional) establishes the joint limits to the joint control system (8) through the user interface system (16).
  d. Automatic: the exoskeleton, through the on board sensory system (3), determines the joint range of the user and communicates the joint limits to the joint control system (8) preferably as part of a self-check program.

or any combination of these.

The invention claimed is:

1. An exoskeleton for assisting human movement that comprises a mechanical structure, wherein the mechanical structure comprises:
   segments joined by joints, the segments including left and right hip segments, left and right upper leg segments, left and right lower leg segments and left and right foot segments that enable a relative movement, between two or more successive segments, for moving left and right lower limbs of a user, respectively; and
   a fastening system for coupling the mechanical structure to the user,
   wherein the fastening system comprises
      a rigid lumbar reinforcement,
      two rotation shafts connected to the left and right hip segments, respectively, and
      two fastening bars rotatably connected to the rotation shafts, respectively,
   wherein a first one of the fastening bars is fixed to the lumbar reinforcement, and a second one of the fastening bars is releasably connected to the lumbar reinforcement via a coupling system such that,
   during use of the exoskeleton, the fastening bars are both connected to the lumbar reinforcement with the lumbar reinforcement occupying a rear portion of the exoskeleton, and
   during a process for decoupling the exoskeleton from the user, the second one of the fastening bars is disconnected from the lumbar reinforcement and is rotated so as to be in a first plane parallel to a sagittal plane, and then the lumbar reinforcement is retracted by being rotated so as to be in a second plane parallel to the sagittal plane.

2. The exoskeleton for assisting human movement according to claim 1 comprising at least 6 degrees of movement in each lower limb of the user, the at least 6 degrees of movement being the following:
   flexion and extension of a hip of the user by rotating in a plane parallel to the sagittal plane;
   abduction-adduction of the hip of the user by rotating in a lateral plane,
   rotation of the hip of the user by rotating in a transverse plane;
   flexion and extension of a knee of the user by rotating in the sagittal plane;
   flexion and extension of an ankle of the user by rotating in the sagittal plane; and
   eversion and inversion of the ankle of the user by rotating in the lateral plane,
   and wherein each of the at least 6 degrees of movement is actuated by a respective actuator.

3. The exoskeleton for assisting human movement according to claim 2, wherein the mechanical structure comprises a shaft eccentric with respect to a crossing of an axis of an upper segment and an axis of a lower segment of a knee joint of the exoskeleton, wherein the shaft is actuated by a knee flexion/extension joint actuator, which defines the degree of movement of flexion and extension of the knee of the user by rotating in a plane parallel to the sagittal plane.

4. The exoskeleton for assisting human movement according to claim 2, wherein the mechanical structure comprises:
   a bar mechanism connected to an ankle flexion/extension joint actuator, wherein the bar mechanism is configured to transmit movement to the ankle of the user; and
   an elastic element configured to exert traction on bars of the bar mechanism so as to contribute to a plantar flexion of the ankle of the user such that, during use,
      in a support phase of a walking motion a weight of the user and action of the ankle flexion/extension joint actuator overcome a counter-torque generated by the elastic element,
      in a lift-off phase of the walking motion the weight of the user is counteracted and a combined action of the elastic element and the ankle flexion/extension joint actuator cause a plantar flexion generating power for an impulse, and
      in a foot transfer phase of the walking motion the ankle flexion/extension joint actuator is configured to counteract the force of the elastic element and generate dorsal flexion of the ankle of the user to prevent impact with a ground.

5. The exoskeleton for assisting human movement according to claim 1, wherein the mechanical structure comprises a condylar fitting mechanism configured to fit a condylar angle formed between a femur and tibia of the user.

6. The exoskeleton for assisting human movement according to claim 5, wherein the condylar fitting mechanism comprises a proximal segment adjacent to a knee joint of the exoskeleton and a distal segment separated from the knee joint of the exoskeleton, wherein the proximal segment is shorter than the distal segment and is introduced into the distal segment, and wherein the proximal and distal segments are joined by a pin arranged such that an axis of the pin is perpendicular to an axis of the tibia of the user and extends in a posteroanterior direction.

7. The exoskeleton for assisting human movement according to claim 5, wherein the condylar fitting mechanism comprises a four-bar mechanism arranged under the knee joint of the exoskeleton.

8. The exoskeleton for assisting human movement according to claim 1, wherein the fastening system further comprises an ischiatic support comprising a girth, wherein a tension of the girth is adjusted through a manual or automatic tensioning mechanism.

9. The exoskeleton for assisting human movement according to claim 1, wherein the fastening system further comprises a device for permanently or detachably anchoring to a shoe of the user.

10. The exoskeleton for assisting human movement according to claim 1, further comprising:
an on board power system that provides energy to an actuation system made up of actuators of the mechanical structure and a computing system;
an on board sensory system that monitors movement of the exoskeleton and comprises at least one of the following subsystems
a proprioceptive subsystem that instantly determines a state of the exoskeleton,
a physiological subsystem which determines a state of the user by biomarkers,
an exteroceptive subsystem which determines a state of the surroundings instantly or over a period of time, and
a perceptive subsystem for exoskeleton-user-surroundings interaction, which determines a state of a mutual interaction between the proprioceptive, physiological and exteroceptive subsystems; and
a movement control system that receives information from the on board sensory system, and comprises one or more of the following subsystems
a joint control system,
a limb control system, and
a control system adapted to control a center of mass of an exoskeleton-user assembly formed by the exoskeleton and the user.

11. The exoskeleton for assisting human movement according to claim 10, wherein the joint control system comprises an impedance control module that receives information from the on board sensory system, and from the physiological subsystem, and automatically adapts the movement of a joint of the exoskeleton to a range, rigidity and spasticity of a joint of the user located adjacent to the joint of the exoskeleton.

12. The exoskeleton for assisting human movement according to claim 10, further comprising a user interface system that interprets a movement intention of the user and transmits the movement intention to the control system of the center of mass.

13. The exoskeleton for assisting human movement according to claim 12, further comprising a communication system that acts as a link between the subsystems of the movement control system, the on board sensory system and the user interface system or between any combination thereof, and wherein one or more on board processing units carry out all computational processing of one or more of the on board sensory system, the subsystems of the movement control systems and the user interface system.

14. The exoskeleton for assisting human movement according to claim 13, wherein the joints of the exoskeleton joining the segments of the mechanical structure comprise a joint range adjustable and adaptable to a joint range of the user, wherein a regulation of the joint range of the joints of the exoskeleton comprises one or more from the following group:
mechanical regulation through a stop or sliding brake, threading, or a linear displacement system;
electronic regulation by limit sensors;
programmed by establishing joint limits to the joint control system through the user interface system; and
automatic regulation by determining the joint range of the user and communicating the joint limits to the joint control system through the on board sensory system.

\* \* \* \* \*